(12) United States Patent
Chen

(10) Patent No.: US 11,021,454 B2
(45) Date of Patent: Jun. 1, 2021

(54) TYPE OF ARYL BENZOFURAN AMIDATED DERIVATIVE AND MEDICAL USE THEREOF

(71) Applicant: CHINA PHARMACEUTICAL UNIVERSITY, Nanjing (CN)

(72) Inventor: Jun Chen, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 211 days.

(21) Appl. No.: 16/075,370

(22) PCT Filed: Jan. 19, 2017

(86) PCT No.: PCT/CN2017/071614
§ 371 (c)(1),
(2) Date: Aug. 3, 2018

(87) PCT Pub. No.: WO2017/133464
PCT Pub. Date: Aug. 10, 2017

(65) Prior Publication Data
US 2019/0040029 A1    Feb. 7, 2019

(30) Foreign Application Priority Data
Feb. 3, 2016 (CN) .......................... 201610076098.8

(51) Int. Cl.
C07D 307/80    (2006.01)
C07D 405/12    (2006.01)
C07D 307/86    (2006.01)
A61P 19/06     (2006.01)
B01D 15/26     (2006.01)

(52) U.S. Cl.
CPC ............ C07D 307/80 (2013.01); A61P 19/06 (2018.01); C07D 307/86 (2013.01); C07D 405/12 (2013.01); B01D 15/26 (2013.01)

(58) Field of Classification Search
CPC .................................................. C07D 307/80
USPC ....................................................... 514/469
See application file for complete search history.

(56) References Cited

FOREIGN PATENT DOCUMENTS

| CN | 1778292 A | 5/2006 |
|---|---|---|
| CN | 102423310 A | 4/2012 |
| CN | 105859667 A | 8/2016 |

OTHER PUBLICATIONS

Hongjin Tang, et al; Synthesis and evaluation of xanthine oxidase inhibitory and antioxidant activities of 2-arylbenzo [b]furan derivatives based on salvianolic acid C; European Journal of Medicinal Chemistry; Aug. 2016, ISSN: 0223-5234, p. 637-648, vol. 124.
Jianming Zhang, et al; Study on hyperuricemia in the physical examination population in Zhengzhou area; Journal of Zhengzhou University (Medical Sciences); 2009, p. 174, vol. 44, issue 1.
Yu Wang,et al; A new drug for the treatment of gout and hyperuricemia—Febuxostat; China Pharmacy; 2009, p. 1748-1750, vol. 20, issue 22.
Xinrong Wu, et al; Research advances on drug therapy targets in hyperuricemia; Chinese Pharmacological Bulletin; 2010, p. 1414-1417, vol. 26, issue 11.
Da Zhou, et al; Research progress on flavonoids as enzymatic inhibitors; Food Science and Technology; 2009, p. 174-178, vol. 34, issue 6.
Jing Zhang; Anti-gout new drug—Febuxostat; Chin Pharm J, 2010, p. 1197-1198, vol. 45, issue 15.
Hao Wu; Survey on synthesis of salvianolic acids and their analogues; Journal of Shenyang Pharmaceutical University,2006, p. 60-64, vol. 23, issue 1.
Weiwei Zhang; Advances in studies on antitum or activities of compounds in Salvia miltiorrhiza; China Journal of Chinese Materia Medica; 2010, p. 389-392, vol. 35, issue 3.
Guanhua Du; Research progress on salvianolic acid, a water-soluble active ingredient of Salvia miltiorrhiza; Basic Medical Sciences and Clinics; 2000, p. 10-14, vol. 20, issue 5.
Yuting Yan; Metabolites of salvianolic acid C in rats in vivo; Journal of China Pharmaceutical University; 2013, p. 442-446, vol. 44, issue 5.
Wenchen Pu; Bioactivities and Synthetic Methods of 2—Arylbenzo[b]furans; Chinese Journal of Organic Chemistry; 2011, p. 155-165, vol. 31.

*Primary Examiner* — Taina D Matos Negron
(74) *Attorney, Agent, or Firm* — Bayramoglu Law Offices LLC

(57) ABSTRACT

The present invention relates to a type of aryl benzofuran amidated derivatives, the medical use thereof, and the preparation method; said derivatives have antioxidation activity, and xanthine oxidase inhibitory activity, and can be used for antioxidation and for preparing compositions, drugs and health products and treating gout and hyperuricemia.

8 Claims, 2 Drawing Sheets

US 11,021,454 B2

TYPE OF ARYL BENZOFURAN AMIDATED DERIVATIVE AND MEDICAL USE THEREOF

CROSS REFERENCE TO RELATED APPLICATIONS

This application is the national phase entry of International Application No. PCT/CN2017/071614, filed on Jan. 19, 2017, which is based upon and claims priority to Chinese Patent Application No. 201610076098.8, filed on Feb. 3, 2016, the entire contents of which are incorporated herein by reference.

TECHNICAL FIELD

The present invention belongs to the field of medicinal chemistry, and in particular, it relates to an aryl benzofuran amidated derivative and its preparation method, said derivative has antioxidation activity, said derivative has xanthine oxidase inhibitory activity, and said derivative can be used for preparing compositions, drugs and health products for preventing and treating gout and hyperuricemia.

BACKGROUND

With the continuous improvement of the living standards, our lifestyle and diet structure have also undergone great changes. Excessive intake of sputum and protein diet has led to a gradual increase in the prevalence of hyperuricemia and gout, which have become two common diseases, frequently occurring. Gout is often associated with other metabolic diseases, such as coronary heart disease, hypertension, hyperlipidemia, diabetes, etc., causing serious harm to our health and property (Zhang Jianming, *Journal of Zhengzhou University*, 2009, 44(1): 174). Gout, as a metabolic disease that seriously affects public health, is increasing gradually in China, especially in the south, where its occurrence is showing a gradual upward trend, so its prevention work has also attracted great attention, and people need imminent safe and effective treatment methods and drugs. Gout is a kind of crystalline arthritis caused by the disorder of sputum metabolism and/or reduced uric acid excretion in biological organisms, and is mainly characterized clinically by hyperuricemia and characteristic acute arthritis, tophi, and chronic gouty arthritis caused by urate crystal deposition, and can lead to urate kidney disease, urinary acid urinary tract stones and other diseases (Wang Yu, *China Pharmacy*, 2009, 20 (22): 1748-1750).

Hyperuricemia is an important physiological and biochemical basis for inducing gout, and its main manifestation is that the serum uric acid concentration is too high, which is caused by two main reasons: one is excessive production of uric acid, and the other is reduced uric acid excretion. Persistent hyperuricemia is a precursor and a potential cause of gout. Therefore, treating hyperuricemia in patients with gout plays a pivotal role in the treatment of gout (Wu Xinrong, *Chinese Journal of Pharmacology*, 2010, 26(11): 1414-1417). However, xanthine Oxidase (XOD) is a key enzyme in the synthesis of uric acid and is one of the important drug targets for the treatment of hyperuricemia. XOD is a complex flavinase, composed of two identical subunits, present in a variety of organisms and is an essential enzyme in the metabolism of nucleic acids in the body. It is widely distributed in the cytoplasm of human heart, liver, lung and other tissues, can catalyze the formation of xanthine in hypoxanthine, and further catalyze the oxidation of xanthine to produce uric acid and superoxide anion (Zhou Da, *Food Science and Technology*, 2009, 34(6):174-178). Before Febuxostat was put on the market, Allopurinol was the only drug that could be used clinically to inhibit the production of uric acid, but it had toxic side effects such as liver and kidney function damage. Febuxostat is a new anti-gout drug approved by the US FDA for long-term control of hyperuricemia in patients with gout. It is a highly selective xanthine oxidase inhibitor that neither acts on other related enzymes in the purine and pyrimidine metabolic pathways, nor affects the normal metabolism of purines and pyrimidines in the body, however, it is also associated with adverse reactions such as abnormal liver function, joint pain, etc., which affects its clinical application to some extent (Zhang Jing, *Chinese Journal of Pharmaceutical Sciences*, 2010, 45(15): 1197-1198). Therefore, the discovery and search for new safe and effective xanthine oxidase inhibitors are of great significance for the treatment of hyperuricemia and gout and other related diseases and for human metabolism research.

Natural products have always been an important source of drugs for the treatment of various diseases, such as cardiovascular drugs like ligustrazine, sodium ferulate and vinpocetine, etc., and anti-tumor drugs like podophyllotoxin, paclitaxel, etc., which are derived from natural products. In addition, some natural products have poor water solubility, severe toxic and side effects, rapid metabolism in the body, and short biological half-life, etc., but after structural optimization, they have become first-line drugs for clinical use, such as Tanshinone IIA sulfonate, Etoposide, Docetaxel, etc. Therefore, proper structural modification of the active ingredients in natural products is an important way to develop new drugs.

*Salvia miltiorrhiza* is the dry root and rhizome of *Salvia miltiorrhiza* Bge., which is distributed in most parts of the country. *Salvia miltiorrhiza* has many functions such as promoting blood circulation, regulating menstruation and relieving pain, clearing heat and soothing the nerves, and is a blood-activating and stasis-relieving medicine commonly used by traditional Chinese medicine. It is used for chest pain, heartache, abdominal pain, sputum accumulation, sputum pain, restlessness, sleeplessness, irregular menstruation, dysmenorrhea, sores ulceration (*People's Republic of China Pharmacopoeia* (2010 edition)). *Salvia miltiorrhiza* preparation has significant curative effect on many diseases and is widely used in the treatment of coronary heart disease, hypercholesterolemia, hypertension, arrhythmia, hepatitis, peripheral vascular disease, pulmonary vascular disease, cirrhosis and other diseases (Wu Hao, *Journal of Shenyang Pharmaceutical University*, 2006, 23(1): 60-64). According to the nature of the chemical constituents of *Salvia miltiorrhiza*, it can be divided into two main categories: water-soluble components and fat-soluble components. The fat-soluble components are mainly concentrated in diterpenoids represented by tanshinone, while the water-soluble components have a phenolic acid structure, which is one of the main material foundations for *Salvia miltiorrhiza* to exert good pharmacological effects, and has been extensively studied in terms of its chemical composition, pharmacokinetics and pharmacology (Zhang Weiwei, *Chinese Journal of Traditional Chinese Medicine*, 2010, 35(3): 389-392). Studies have shown that salvianolic acid components exert pharmacological effects through various mechanisms of action, such as inhibiting platelet aggregation, antithrombotic formation, preventing atherosclerotic plaque formation, inhibiting endogenous cholesterol synthesis, scavenging free radicals, and protecting the body by reducing the damage of free radicals to the body (Du Guanhua, *Basic Medicine and Clinical Medicine*, 2000, 20(5): 10-14).

The water-soluble component originally isolated from Danshensu (β-3,4-dihydroxyphenyllactic acid) is the basic chemical structure of various salvianolic acids (Du Guanhua, *Basic Medicine and Clinical Medicine*, 2000, 20(5): 10-14), such as salvianolic acid A is formed by the condensation of one molecule of Danshensu with two molecules of caffeic acid, and salvianolic acid B is a combination of three molecules of Danshensu and one molecule of caffeic acid, while salvianolic acid C is formed by the condensation of two molecules of Danshensu. Other phenolic compounds in *Salvia miltiorrhiza* also include salvianolic acid D, salvianolic acid E, salvianolic acid F, salvianolic acid G, salvianolic acid H, salvianolic acid I, rosmarinic acid, lithosperic acid and the like. Zhu Dayuan et al. found that the phenolic acids such as salvianolic acid B, lithospermic acid, rosmarinic acid and danshensu in *Salvia miltiorrhiza* have the inhibitory effect of xanthine oxidase and can reduce the serum uric acid level in mice with hyperuricemia (CN). 200410084620.4).

Our previous study found that salvianolic acid C has strong xanthine oxidase inhibitory activity and its inhibitory effect is superior to salvianolic acid A (Yan Yuting, *Journal of China Pharmaceutical University*, 2013, 44(5): 442-446). Salvianolic acid C can be used as a xanthine oxidase inhibitor for the prevention and treatment of gout and hyperuricemia and its complications (CN 201210000772.6).

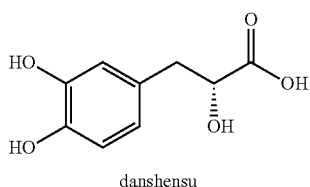

danshensu

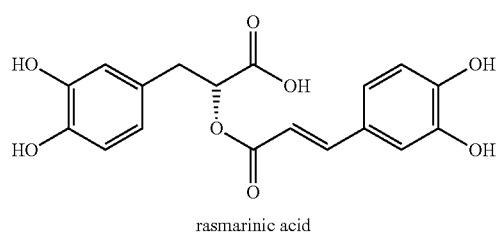

rasmarinic acid

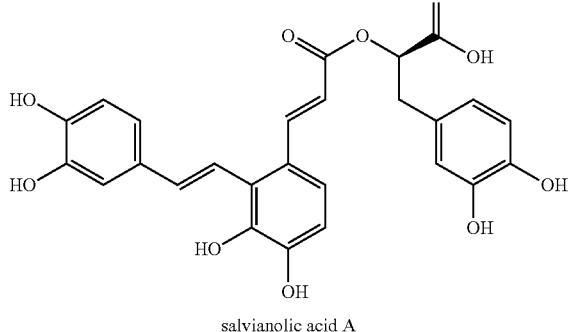

salvianolic acid A

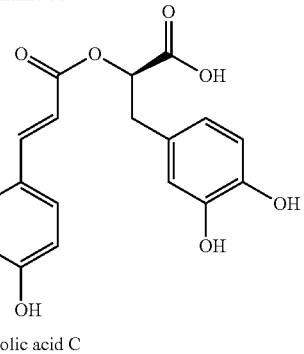

salvianolic acid C

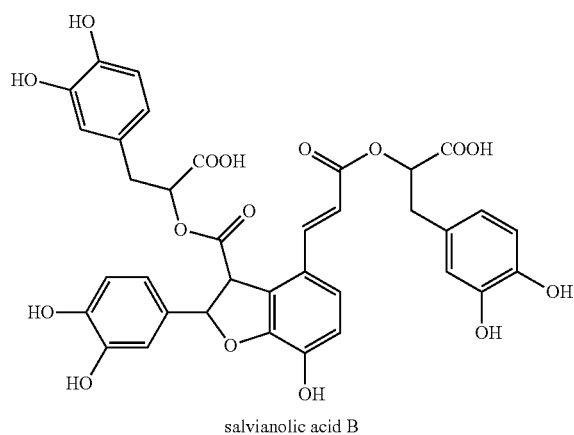

salvianolic acid B

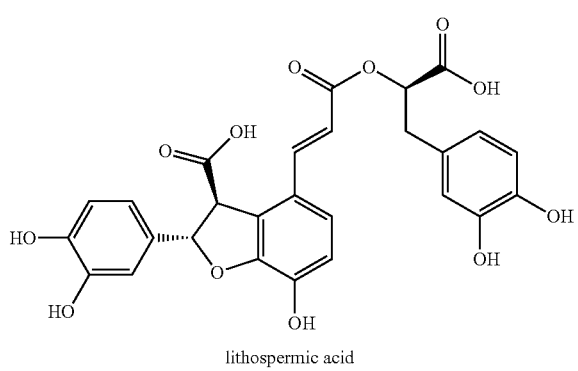 [SMILES: O=C(/C=C/c1ccc(O)c2c1[C@H](C(=O)O)[C@@H](c1ccc(O)c(O)c1)O2)O[C@H](Cc1ccc(O)c(O)c1)C(=O)O]

lithospermic acid

Yan Yuting et al. studied the metabolism of salvianolic acid C in rats, used HPLC-QTOF-MS/MS method to detect five metabolites from rat blood and urine, and preliminarily estimated the drug metabolism pathway of salvianolic acid C in rats according to the law of compound cleavage (Yan Yuting, *Journal of China Pharmaceutical University*, 2013, 44(5): 442-446).

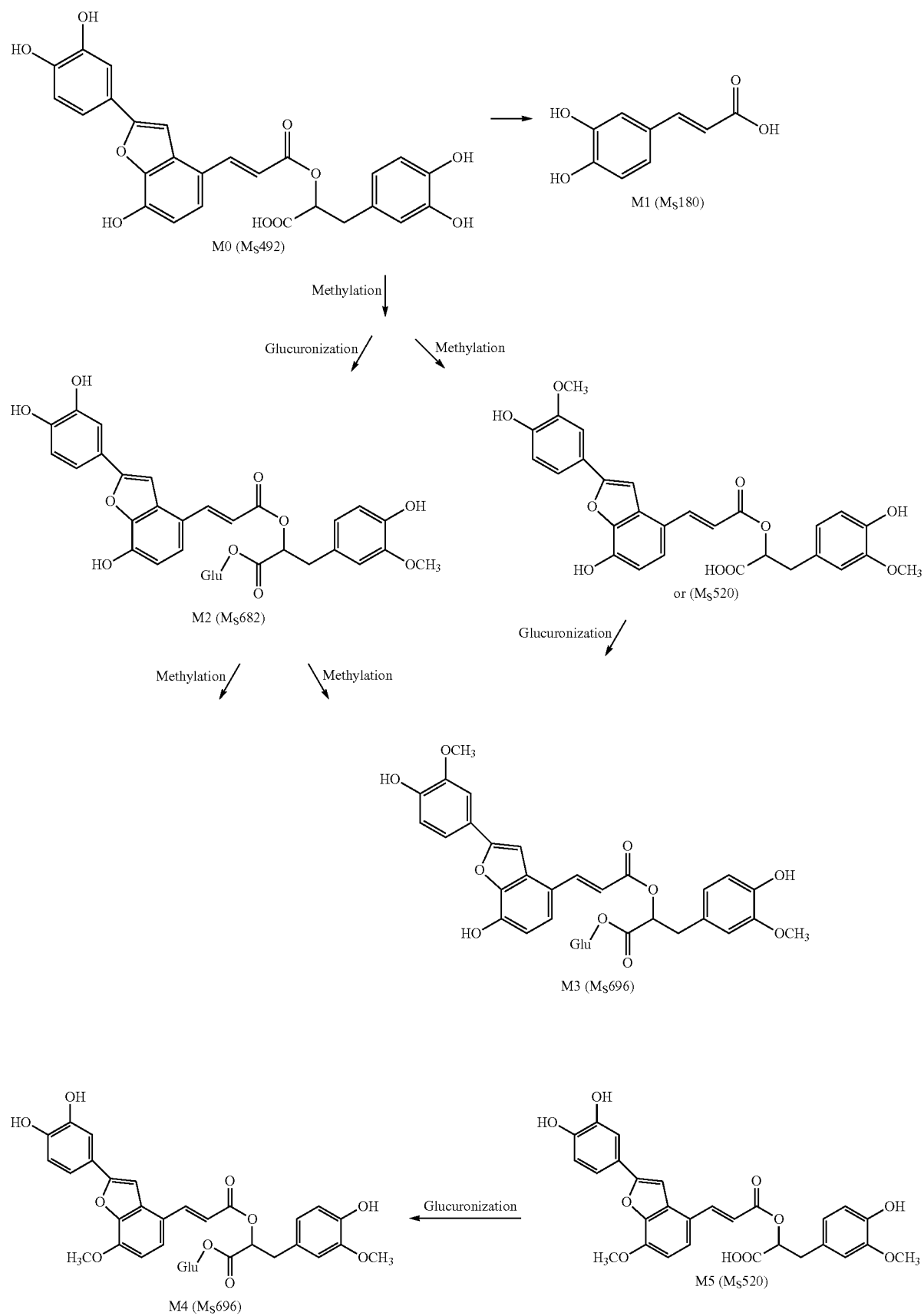

Possible In Vivo Metabolic Pathways of Salvianolic Acid C

In summary, it can be speculated that the structural unit of β-3,4-dihydroxyphenyl lactic acid may have a certain correlation with the inhibitory activity of xanthine oxidase. However, salvianolic acid C also has a structural skeleton of an aryl benzofuran. Aryl benzofurans have long been a hot spot for researchers. It is a class of compounds with a new lignin skeleton type, distributed in a variety of higher plants in nature, and has a wide range of biological activities, such as antiviral, antitumor, antifungal, antioxidant, immunomodulatory and cardiovascular diseases, etc. If we take a look at the research progress of aryl benzofuran compounds in recent years, the research work has focused on the isolation and identification of benzofuran skeleton compounds, the construction and synthesis of derivative libraries, the study of structure-activity relationship, and in-depth study on the screening and mechanism of biological activity, especially the continuous discovery of new methods for the formation of benzofuran ring (Pu Wenchen, "Bioactivity and Synthesis Strategy of 2-Aryl benzofuran Derivatives", *Organic Chemistry*, 2011, 31, 155-165).

Based on the above, there are still some unknown problems that need to be resolved. (1) What effect does the aryl benzofuran ring have on the biological activity (such as xanthine oxidase inhibitory activity, antioxidant activity) exhibited by a compound having this skeleton type (such as salvianolic acid C, etc.); (2) The effects of substitution by different substituents (such as electron-withdrawing groups, electron-donating groups, etc.) on the pharmacological activities of aryl benzofuran ring compounds are still unknown; that is, the specific structure-activity relationship for specific biological activities remains unclear; (3) Those skilled in the art are still unable to determine whether the structure containing no β-3,4-dihydroxyphenyllactic acid but only the aryl benzofuran compound also has similar biological activity to that of β-3,4-dihydroxyphenyl lactic acid, such as the activity of inhibiting xanthine oxidase; at the same time, it is also unclear to those skilled in the art whether the structure containing no β-3,4-dihydroxyphenyl-lactic acid but only the aryl benzofuran compound also has similar biological activity to that of β-3,4-dihydroxyphenyl lactic acid, such as the activity of inhibiting xanthine oxidase.

In addition, salvianolic acid C is highly water-soluble, sensitive to air, strong acidity, strong alkalinity, etc., with poor physical and chemical stability, and the process in the body is easily metabolized, with a short biological half-life, which limits its clinical application. Therefore, we have designed and synthesized a series of aryl benzofuran derivatives with the core structure of 2-aryl benzofuran ring contained in the structure of salvianolic acid C, and performed in-depth discussion on its related biological activities, which provides certain research value.

SUMMARY

The present invention discloses an aryl benzofuran amidated derivative.

The present invention discloses the antioxidant activity of an aryl benzofuran amidated derivative.

The present invention discloses an aryl benzofuran amidated derivative having the activity of scavenging free radicals.

The present invention discloses an aryl benzofuran amidated derivative having the inhibitory activity of xanthine oxidase.

The present invention discloses an aryl benzofuran amidated derivative having an activity of reducing uric acid.

The present invention discloses an aryl benzofuran amidated derivative having activity for treating or preventing gout.

The present invention discloses an aryl benzofuran amidated derivative for use in the preparation of compositions, medicaments, health care products for treating or preventing gout, and, or, hyperuricemia.

The present invention discloses an aryl benzofuran amidated derivative for use in the preparation of compositions, medicaments and health care products for treating or preventing gout and hyperuricemia.

The present invention discloses a preparation method of an aryl benzofuran amidated derivative.

The present invention discloses an aryl benzofuran amidated derivative.

The invention discloses an aryl benzofuran amidated derivative, the structural formula of which is as shown in Formula I:

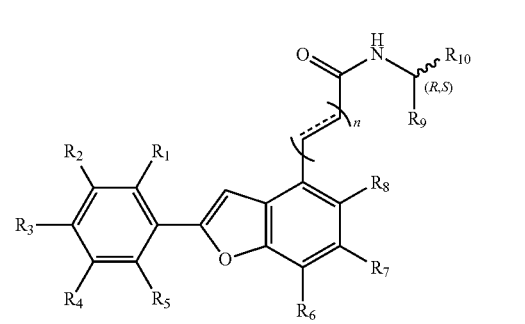

$R_1$, $R_2$, $R_3$, $R_4$, $R_5$, $R_6$, $R_7$, $R_8$ are each independently hydrogen, hydroxy, halogen, nitro, benzyl, $C_{1-4}$ alkyl unsubstituted or substituted with 1 to 3 substituents selected from halogen, hydroxy, nitro and $C_{1-2}$ alkoxy, $C_{1-3}$ alkoxy unsubstituted or substituted by 1 to 2 substituents selected from halogen, hydroxy, nitro and $C_{1-2}$ alkoxy;

$R_9$ is hydrogen, $C_{1-4}$ alkyl which is unsubstituted or substituted with 1 to 3 substituents selected from halogen, hydroxy, decyl, $C_{1-3}$ alkyl and $C_{1-2}$ alkoxy, 3-ethyl-1H-indole which is unsubstituted or substituted by halogen and hydroxy, phenyl which is unsubstituted or substituted by halogen, hydroxy and $C_{1-2}$ alkoxy, benzyl which is unsubstituted or substituted by halogen, hydroxy and $C_{1-2}$ alkoxy, other aryl groups which are unsubstituted or substituted by halogen, hydroxy and $C_{1-2}$ alkoxy (wherein said halogen X=F, Cl, Br, n=1, 2, 3), such as 3, 4-dihydroxybenzyl, 3, 4-dimethoxybenzyl, 4-hydroxybenzyl, 4-methoxybenzyl, etc.;

$R_{10}$ is hydrogen, —COOH, —COOCH$_3$, —COOCH$_2$CH$_3$, —COOCH(CH$_3$)$_2$, —COO(CH$_2$)$_2$CH$_3$ or $C_{1-4}$ alkyl that is substituted by 1~3 substituents selected from halogen, hydroxy, $C_{1-3}$ alkyl, and $C_{1-2}$ alkoxy.

The present invention discloses an aryl benzofuran amidated derivative as shown in Formula I that is characterized by that:

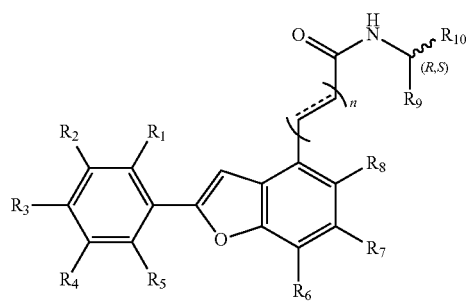

I

Wherein: $R_3$, or, and, $R_4$ are substituents other than hydroxy;

Wherein: $R_9$, or, and, $R_{10}$ are substituents other than hydrogen;

The invention discloses a type of aryl benzofuran amidated derivative, the structural formula of which is as shown in Formula II:

II $R_1$ = H, OH, X, $CH_3$, $OCH_3$
$R_2$ = H, OH, X, $CH_3$, $OCH_3$
$R_3$ = H, OH, X, $CH_3$, $OCH_3$
$R_4$ = H, OH, X, $CH_3$, $OCH_3$
$R_5$ = H, OH, X, $CH_3$, $OCH_3$
$R_6$ = H, $CH_3$, $CH_2CH_3$, $CH(CH_3)_2$, $(CH_2)_2CH_3$
X = F, Cl, Br
n = 1, 2, 3

The invention discloses a type of aryl benzofuran amidated derivative, the structural formula of which is as shown in Formula III:

III $R_1$ = H, OH, X, $CH_3$, $OCH_3$
$R_2$ = H, OH, X, $CH_3$, $OCH_3$
$R_3$ = H, OH, X, $CH_3$, $OCH_3$
$R_4$ = H, OH, X, $CH_3$, $OCH_3$
$R_5$ = H, OH, X, $CH_3$, $OCH_3$
$R_6$ = H, $CH_3$, $CH_2CH_3$, $CH(CH_3)_2$, $(CH_2)_2CH_3$
X = F, Cl, Br
n = 1, 2, 3

The invention discloses an aryl benzofuran amidated derivative, the structural formula of which is as shown in Formula IV:

IV $R_1$ = H, OH, X, $CH_3$, $OCH_3$
$R_2$ = H, OH, X, $CH_3$, $OCH_3$
$R_3$ = H, OH, X, $CH_3$, $OCH_3$
$R_4$ = $CH_3$, $OCH_3$, $CH_2CH_3$, $CH(CH_3)_2$, $(CH_2)_2CH_3$
$R_5$ = H, $CH_3$, $CH_2CH_3$, $CH(CH_3)_2$, $(CH_2)_2CH_3$
X = F, Cl, Br
n = 1, 2, 3

The invention discloses a type of aryl benzofuran amidated derivative, the structural formula of which is as shown in Formula V:

V

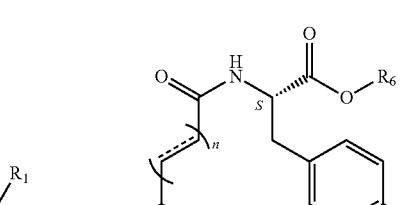

R$_1$ = H, OH, X, CH$_3$, OCH$_3$
R$_2$ = H, OH, X, CH$_3$, OCH$_3$
R$_3$ = H, OH, X, CH$_3$, OCH$_3$
R$_4$ = CH$_3$, OCH$_3$, CH$_2$CH$_3$, CH(CH$_3$)$_2$, (CH$_2$)$_2$CH$_3$
R$_5$ = H, CH$_3$, CH$_2$CH$_3$, CH(CH$_3$)$_2$, (CH$_2$)$_2$CH$_3$
X = F, Cl, Br
n = 1, 2, 3

The invention discloses a type of aryl benzofuran amidated derivative, the structural formula of which is as shown in Formula VI:

VI

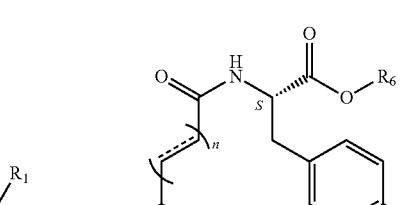

R$_1$ = H, OH, X, CH$_3$, OCH$_3$
R$_2$ = H, OH, X, CH$_3$, OCH$_3$
R$_3$ = H, OH, X, CH$_3$, OCH$_3$
R$_4$ = H, OH, X, CH$_3$, OCH$_3$
R$_5$ = H, OH, X, CH$_3$, OCH$_3$
R$_6$ = H, CH$_3$, CH$_2$CH$_3$, CH(CH$_3$)$_2$, (CH$_2$)$_2$CH$_3$
X = F, Cl, Br
n = 1, 2, 3

The invention discloses a type of aryl benzofuran amidated derivative, the structural formula of which is as shown in Formula VII:

VII

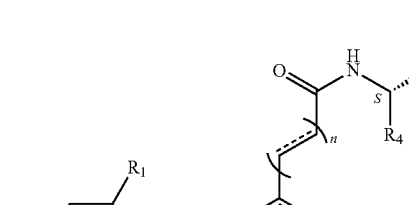

R$_1$ = H, OH, X, CH$_3$, OCH$_3$
R$_2$ = H, OH, X, CH$_3$, OCH$_3$
R$_3$ = H, OH, X, CH$_3$, OCH$_3$
R$_4$ = H, OH, X, CH$_3$, OCH$_3$
R$_5$ = H, OH, X, CH$_3$, OCH$_3$
R$_6$ = H, CH$_3$, CH$_2$CH$_3$, CH(CH$_3$)$_2$, (CH$_2$)$_2$CH$_3$
X = F, Cl, Br
n = 1, 2, 3

The invention discloses a type of aryl benzofuran amidated derivative, the structural formula of which is as shown in Formula VIII:

VIII

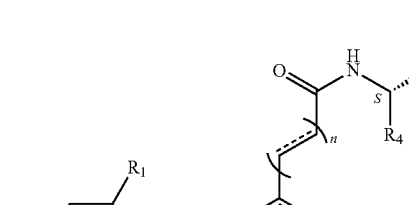

R$_1$ = H, OH, X, CH$_3$, OCH$_3$
R$_2$ = H, OH, X, CH$_3$, OCH$_3$
R$_3$ = H, OH, X, CH$_3$, OCH$_3$
R$_4$ = CH$_3$, OCH$_3$, CH$_2$CH$_3$, CH(CH$_3$)$_2$, (CH$_2$)$_2$CH$_3$
R$_5$ = H, CH$_3$, CH$_2$CH$_3$, CH(CH$_3$)$_2$, (CH$_2$)$_2$CH$_3$
X = F, Cl, Br
n = 1, 2, 3

The invention discloses an aryl benzofuran amidated derivative, the structural formula of which is as shown in Formula IX:

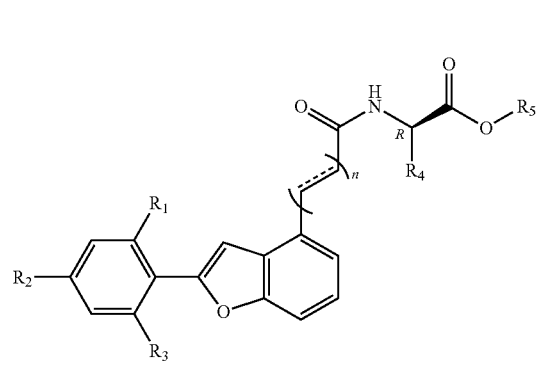

IX

R₁ = H, OH, X, CH₃, OCH₃
R₂ = H, OH, X, CH₃, OCH₃
R₃ = H, OH, X, CH₃, OCH₃
R₄ = CH₃, OCH₃, CH₂CH₃, CH(CH₃)₂, (CH₂)₂CH₃
R₅ = H, CH₃, CH₂CH₃, CH(CH₃)₂, (CH₂)₂CH₃
X = F, Cl, Br
n = 1, 2, 3

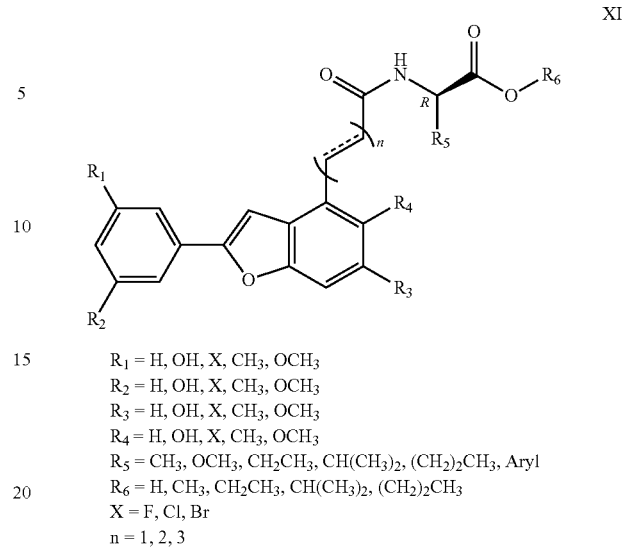

XI

R₁ = H, OH, X, CH₃, OCH₃
R₂ = H, OH, X, CH₃, OCH₃
R₃ = H, OH, X, CH₃, OCH₃
R₄ = H, OH, X, CH₃, OCH₃
R₅ = CH₃, OCH₃, CH₂CH₃, CH(CH₃)₂, (CH₂)₂CH₃, Aryl
R₆ = H, CH₃, CH₂CH₃, CH(CH₃)₂, (CH₂)₂CH₃
X = F, Cl, Br
n = 1, 2, 3

The invention discloses a type of aryl benzofuran amidated derivative, the structural formula of which is as shown in Formula X:

The invention discloses a type of aryl benzofuran amidated derivative, the structural formula of which is as shown in Formula XII:

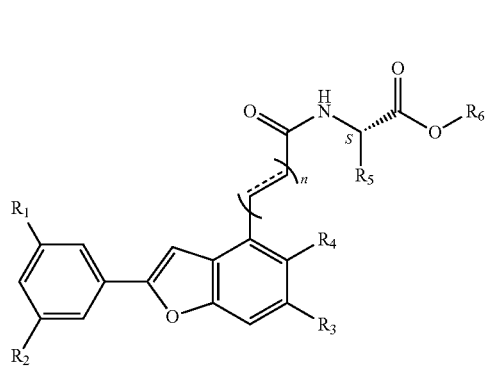

X

R₁ = H, OH, X, CH₃, OCH₃
R₂ = H, OH, X, CH₃, OCH₃
R₃ = H, OH, X, CH₃, OCH₃
R₄ = H, OH, X, CH₃, OCH₃
R₅ = CH₃, OCH₃, CH₂CH₃, CH(CH₃)₂, (CH₂)₂CH₃, Aryl
R₆ = H, CH₃, CH₂CH₃, CH(CH₃)₂, (CH₂)₂CH₃
X = F, Cl, Br
n = 1, 2, 3

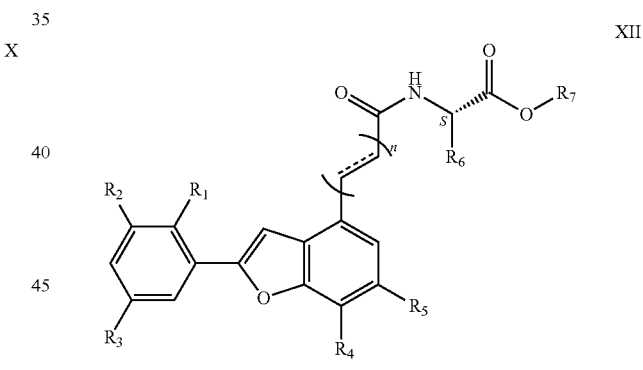

XII

R₁ = H, OH, X, CH₃, OCH₃
R₂ = H, OH, X, CH₃, OCH₃
R₃ = H, OH, X, CH₃, OCH₃
R₄ = H, OH, X, CH₃, OCH₃
R₅ = H, OH, X, CH₃, OCH₃
R₆ = CH₃, OCH₃, CH₂CH₃, CH(CH₃)₂, (CH₂)₂CH₃, Aryl
R₇ = H, CH₃, CH₂CH₃, CH(CH₃)₂, (CH₂)₂CH₃
X = F, Cl, Br
n = 1, 2, 3

The invention discloses a type of aryl benzofuran amidated derivative, the structural formula of which is as shown in Formula XI:

The invention discloses a type of aryl benzofuran amidated derivative, the structural formula of which is as shown in Formula XIII:

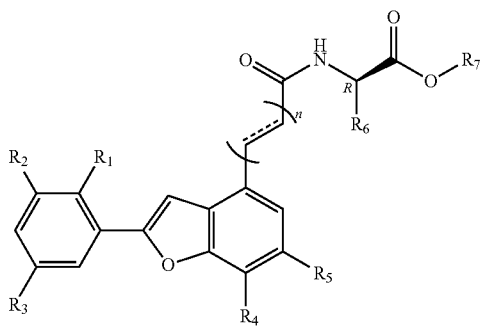

R₁ = H, OH, X, CH₃, OCH₃
R₂ = H, OH, X, CH₃, OCH₃
R₃ = H, OH, X, CH₃, OCH₃
R₄ = H, OH, X, CH₃, OCH₃
R₅ = H, OH, X, CH₃, OCH₃
R₆ = CH₃, OCH₃, CH₂CH₃, CH(CH₃)₂,(CH₂)₂CH₃, Aryl
R₇ = H, CH₃, CH₂CH₃, CH(CH₃)₂, (CH₂)₂CH₃
X = F, Cl, Br
n = 1, 2, 3

The present invention discloses an aryl benzofuran amidated derivative, the structural formula of which is as shown in Formula 1;

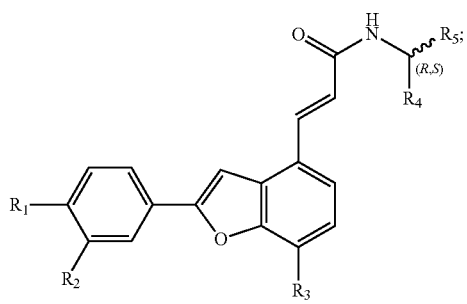

Wherein $R_1$, $R_2$, $R_3$ are each independently $C_{1-4}$ alkyl unsubstituted or substituted by halogen and hydroxy, $C_{1-3}$ alkoxy unsubstituted or substituted by halogen and hydroxy, halogen, nitro, benzyl;

$R_4$ is hydrogen, $C_{1-4}$ alkyl unsubstituted or substituted by halogen, hydroxy and thiol, 3-ethyl-1H-indole, phenyl unsubstituted or substituted by halogen and hydroxy, benzyl unsubstituted or substituted by halogen and hydroxy, other aryls unsubstituted or substituted by halogen and hydroxy (wherein halogen X=F, Cl, Br), such as 3, 4-dihydroxybenzyl, 3, 4-dimethoxybenzyl, 4-hydroxybenzyl, 4-methoxybenzyl, etc.;

$R_5$ is hydrogen, —COOH, —COOCH₃, —COOCH₂CH₃, —COOCH(CH₃)₂, —COO(CH₂)₂CH₃ or hydrogen, $C_{1-4}$ alkyl;

The present invention discloses an aryl benzofuran amidated derivative as shown in Formula 1 that is characterized by that:

The structural formula of which is as shown in Formula 1:

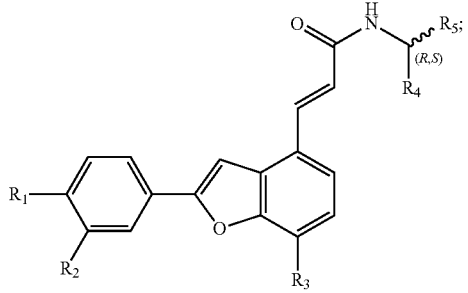

Wherein $R_1$, $R_2$, $R_3$ are each independently hydrogen, hydroxy; $R_4$ is hydrogen; $R_5$ is hydrogen;

The present invention discloses an aryl benzofuran amidated derivative as shown in Formula 1 that is characterized by that:

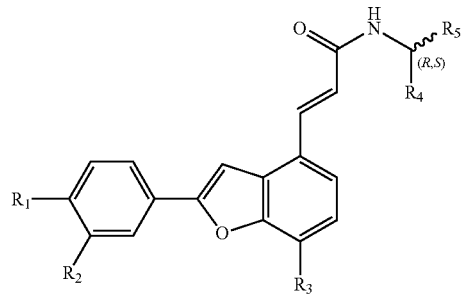

Wherein $R_1$, $R_2$, $R_3$ are each independently $C_{1-4}$ alkyl unsubstituted or substituted by halogen and hydroxy, $C_{1-3}$ alkoxy unsubstituted or substituted by halogen and hydroxy, halogen, nitro, benzyl;

$R_4$ is $C_{1-4}$ alkyl which is unsubstituted or substituted with 1 to 3 substituents selected from halogen, hydroxy and decyl, 3-ethyl-1H-indole which is unsubstituted or substituted by halogen and hydroxy, phenyl which is unsubstituted or substituted by halogen and hydroxy, benzyl which is unsubstituted or substituted by halogen and hydroxy, other aryls which are unsubstituted or substituted by halogen and hydroxy (wherein said halogen X=F, Cl, Br), such as 3, 4-dihydroxybenzyl, 3, 4-dimethoxybenzyl, 4-hydroxybenzyl, 4-methoxybenzyl, etc.;

$R_5$ is —COOH, —COOCH₃, —COOCH₂CH₃, —COOCH(CH₃)₂, —COO(CH₂)₂CH₃ or hydrogen, $C_{1-4}$ alkyl;

The present invention discloses a type of aryl benzofuran amidated derivative, the structural formula of which is as shown in Formula 5a:

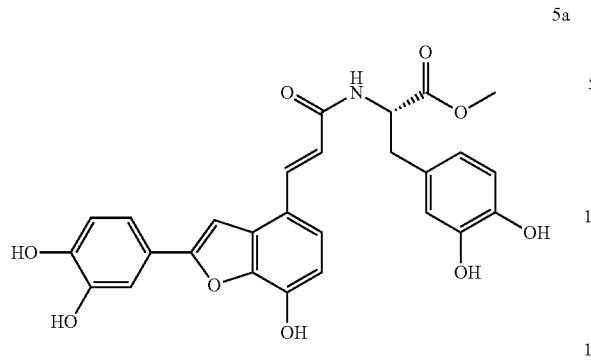

5a

The present invention discloses a type of aryl benzofuran amidated derivative, the structural formula of which is as shown in Formula 6a:

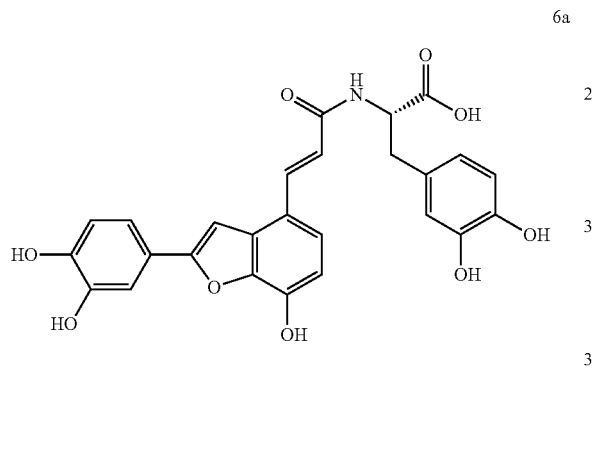

6a

The present invention discloses a type of aryl benzofuran amidated derivative, the structural formula of which is as shown in Formula 5b:

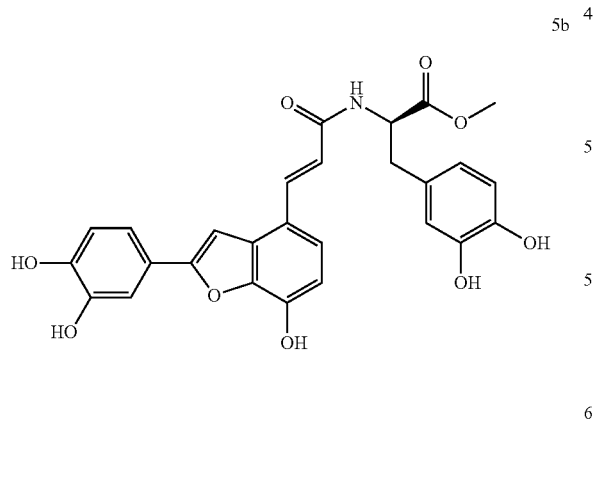

5b

The present invention discloses a type of aryl benzofuran amidated derivative, the structural formula of which is as shown in Formula 6b:

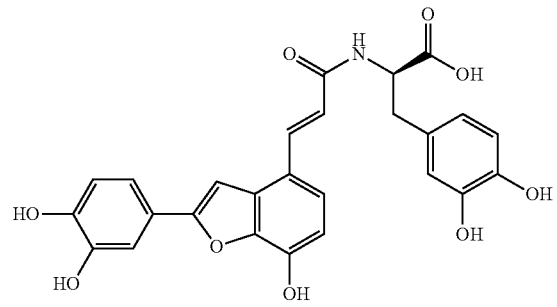

6b

The present invention discloses a type of aryl benzofuran amidated derivative, the structural formula of which is as shown in Formula 5c:

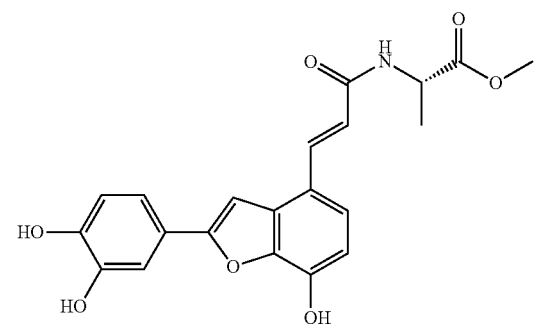

5c

The present invention discloses a type of aryl benzofuran amidated derivative, the structural formula of which is as shown in Formula 6c:

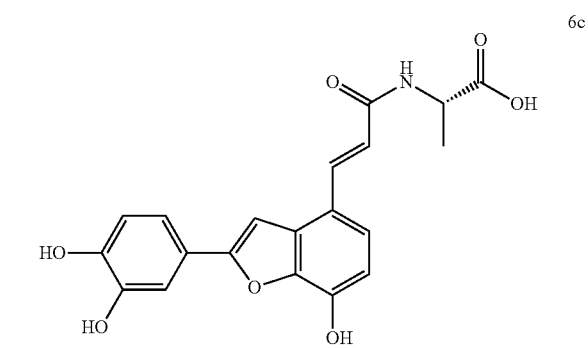 [SMILES: C[C@H](NC(=O)/C=C/c1ccc(O)c2oc(-c3ccc(O)c(O)c3)cc12)C(=O)O]

6c

The present invention discloses a type of aryl benzofuran amidated derivative, the structural formula of which is as shown in Formula 5d:

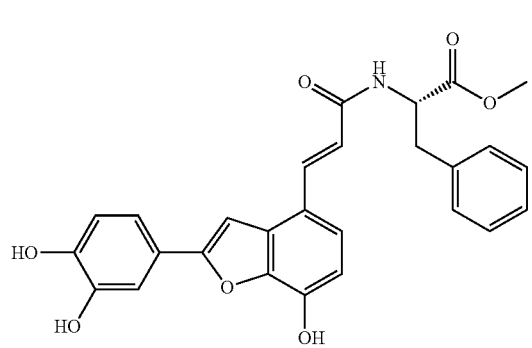

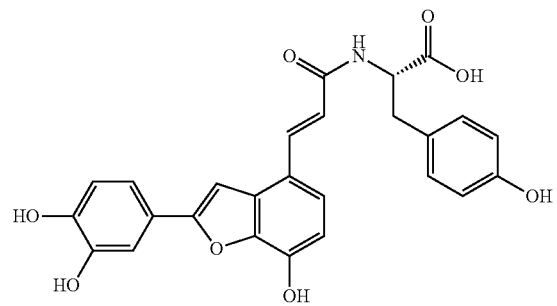

The present invention discloses a type of aryl benzofuran amidated derivative, the structural formula of which is as shown in Formula 6d:

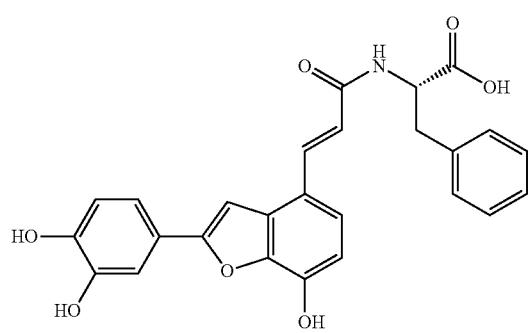

The present invention discloses a type of aryl benzofuran amidated derivative, the structural formula of which is as shown in Formula 5e:

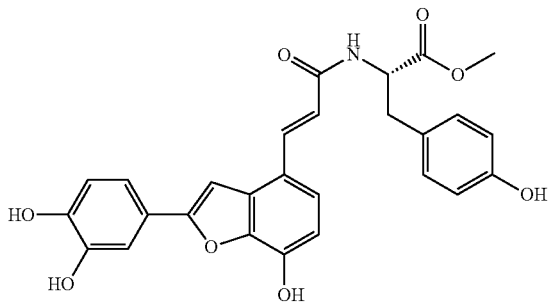

The present invention discloses a type of aryl benzofuran amidated derivative, the structural formula of which is as shown in Formula 6e:

The present invention discloses a type of aryl benzofuran amidated derivative, the structural formula of which is as shown in Formula 5f:

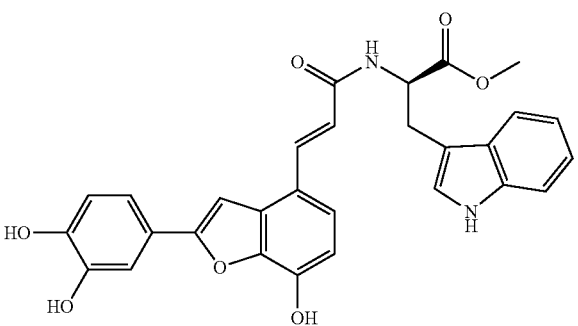

The present invention discloses a type of aryl benzofuran amidated derivative, the structural formula of which is as shown in Formula 6f:

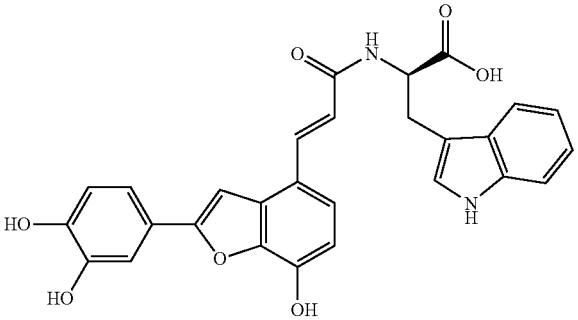

The present invention discloses a type of aryl benzofuran amidated derivative, the structural formula of which is as shown in Formula 7:

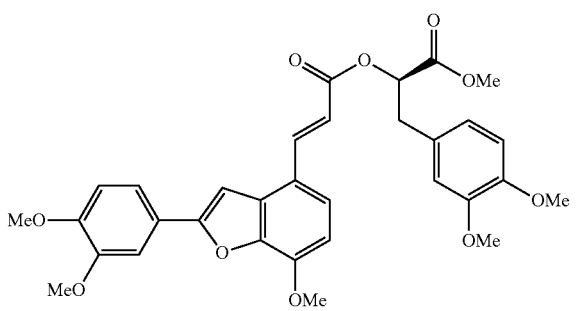

The present invention discloses a type of aryl benzofuran amidated derivative, the structural formula of which is as shown in Formula 9a:

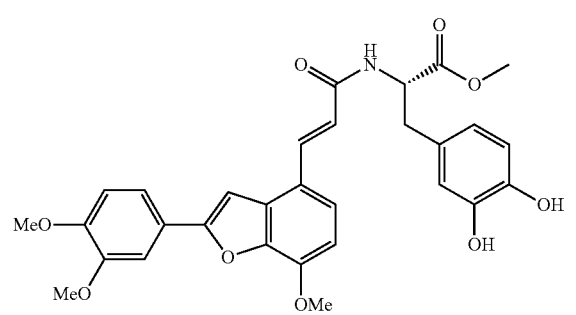

The invention discloses a type of aryl benzofuran amidated derivative, the structural formula of which is as shown in Formula 10a:

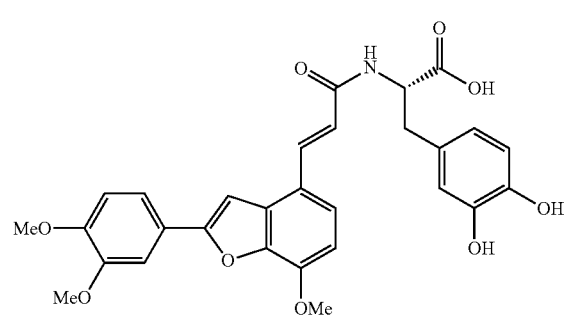

The synthesis method of an aryl benzofuran amidated derivative in the present invention is as follows:

(1) Mix salvianolic acid C with an inorganic base, ultrasonically dissolve it in a mixed solvent, and heat it and continuously detect the reaction; after the reaction is completed, the silica gel column chromatography is carried out to obtain an intermediate Tournefolic acid A (2);

(2) Add $SOCl_2$ to the organic solvent under cooling, and let it react for 30 min, then add amino compounds such as alanine, phenylalanine, cysteine, tyrosine, methionine, tryptophan, and D/L-DOPA, stir it at room temperature, concentrate and evaporate the solvent before washing and drying it to obtain a series of carboxyl-protected amino derivatives;

(3) Mix the intermediate product Tournefolic acid A with a series of amino derivatives at the mole ratio of 1:1.1~2 under the action of a condensing agent, dissolve it in an organic solvent, stir it at room temperature, and after reaction treatment, separate it by silica gel column chromatography to obtain a series of aryl benzofuran amidated derivatives;

(4) Add an inorganic base to the series of aryl benzofuran amidated derivatives, mix the solvent and ultrasonically dissolve it, stir at room temperature or heat it under reflux, and continuously monitor the reaction by TLC, subject the sample mixture to post-treatment, and then pass it through silica gel column chromatography or preparative high-performance liquid chromatography for separation and purification to obtain a series of high purity benzofuran amidated derivatives.

The inorganic alkali hydrolysis in the first step may be LiOH, NaOH, KOH or the like, and the organic solvent is THF, MeOH, H2O or a mixed solvent thereof, preferably a mixed solvent of $MeOH/H_2O$, and the solvent volume ratio is preferably 3:1~5:1, the reaction time is preferably 8~12 h;

The separation and purification method in the first step is specifically: silica gel column chromatography, isocratic eluting with chloroform/methanol/formic acid (10:1:0.1, v/v/v) to obtain the intermediate Tournefolic acid A (2);

The amino compound in the second step is an amino acid of various D/L configurations and other chiral amino derivatives, and the organic solvent is a reagent such as methanol, ethanol or isopropanol, and the reaction time is preferably 18-24 h;

The separation and purification method in the second step is specifically: wash the sample by methanol and diethyl ether alternatively for multiple times, followed by concentrating and evaporating;

The condensing agent in the third step may be DCC/HoBt, EDCI/HoBt, HATU, HBTU, PyBOP, preferably EDCI/HoBt, and the organic solvent is preferably a mixed solvent $DMF/CH_2Cl_2$ (3:1~5:1 v/v), the reaction time is preferably 8~12 h;

The separation and purification method in the third step is specifically: silica gel column chromatography, gradient eluting with chloroform/methanol to obtain the target derivative;

The inorganic base in the fourth step may be LiOH, NaOH, KOH, preferably NaOH, and the organic solvent is THF, MeOH, $H_2O$ or a mixed solvent thereof, preferably $MeOH/H_2O$ (3:1~5:1 v/v), the reaction time is preferably 8 to 12 h.

The specific separation and purification method for part of the aryl benzofuran amidated derivative in the fourth step is as follows: separation and purification by silica gel column chromatography, mobile phase gradient elution with chloroform/methanol/formic acid; or separation and purification of sample mixture with preparative liquid chromatography column, wherein the column is (Agilent, Zorbax-$C_{18}$, 5 μm, 9.4×250 mm), and the chromatographic conditions are preferably: flow rate: 8 mL/min, detection wavelength: 281 nm, column temperature: 30° C., mobile phase: acetonitrile-0.1% formic acid-water.

The compounds obtained in the preparation method herein are all characterized by mass spectrometry and spectroscopy such as nuclear magnetic resonance, with purity detected by HPLC.

The aryl benzofuran amidated derivative of the present invention and a pharmaceutically acceptable salified product thereof can be combined with common medicinal excipient(s) and carrier(s) to prepare compositions for gout and hyperuricemia drugs, thereby preventing or treating these conditions. The above drugs can be made in different forms according to actual needs, such as tablets, injections, suppositories, aerosols, Nano-preparations and the like.

Compared with the prior art, the present invention has the following beneficial effects:

(1) The present invention obtains a series of aryl benzofuran derivatives by chemically modifying the salvianolic acid C as a substrate. The in vitro bioactive screening and cell viability assay have shown that, in general, the aryl benzofuran amidated derivatives of the present invention exhibit strong xanthine oxidase inhibitory activity and antioxidant activity, providing a material basis for the prevention and treatment of gout and hyperuricemia and their complications.

(2) The aryl benzofuran amidated derivatives in present the invention have a novel structure with inhibitory activity against xanthine oxidase. Compared with salvianolic acid C, their water solubility is improved to some extent, and their physicochemical stability is increased to some extent as well, with low toxic and side effects, which provides it certain development and application value.

BRIEF DESCRIPTION OF THE DRAWINGS

FIG. 3 is a combination of Part A, Part B, Part C, Part D, Part E, and Part F, showing the results of docking experiments between different compounds and xanthine oxidase molecules, (A) Febuxostat (B) Allopurinol (C) 6b (D) 6e (E) Salvianolic acid C (1) (F) 5b, respectively.

DETAILED DESCRIPTION OF THE EMBODIMENTS

Figure 1:
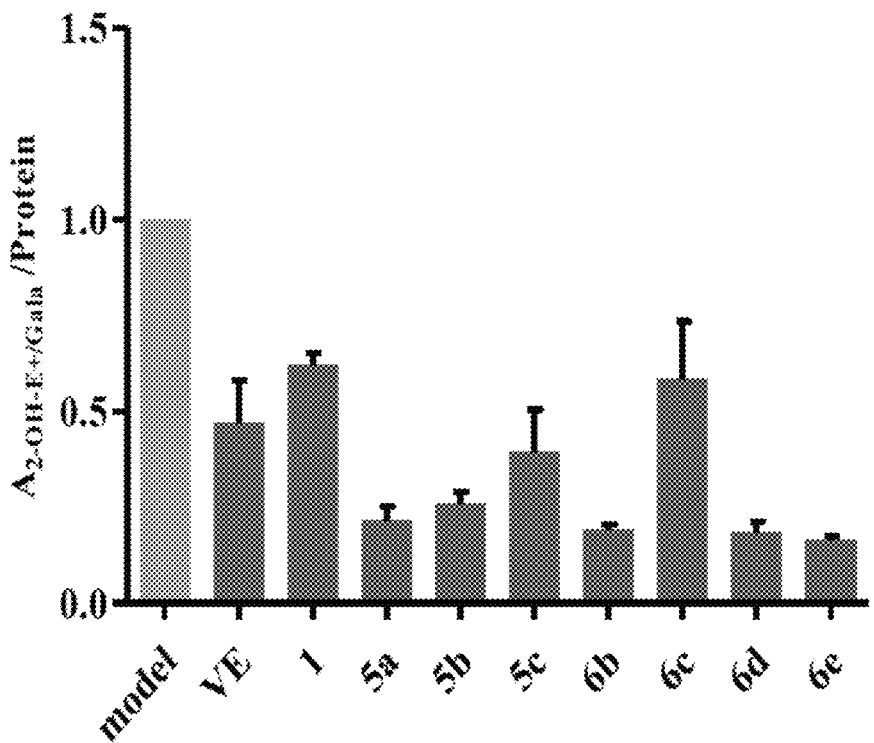
FIG. 1: Scavenging effects of aryl benzofuran amidated derivatives 5a, 5b, 5c, 6b, 6c, 6d, 6e and Salvianolic acid C (1) and Ve on superoxide anion in LPS-stimulated macrophage RAW 264.7
Figure 2:
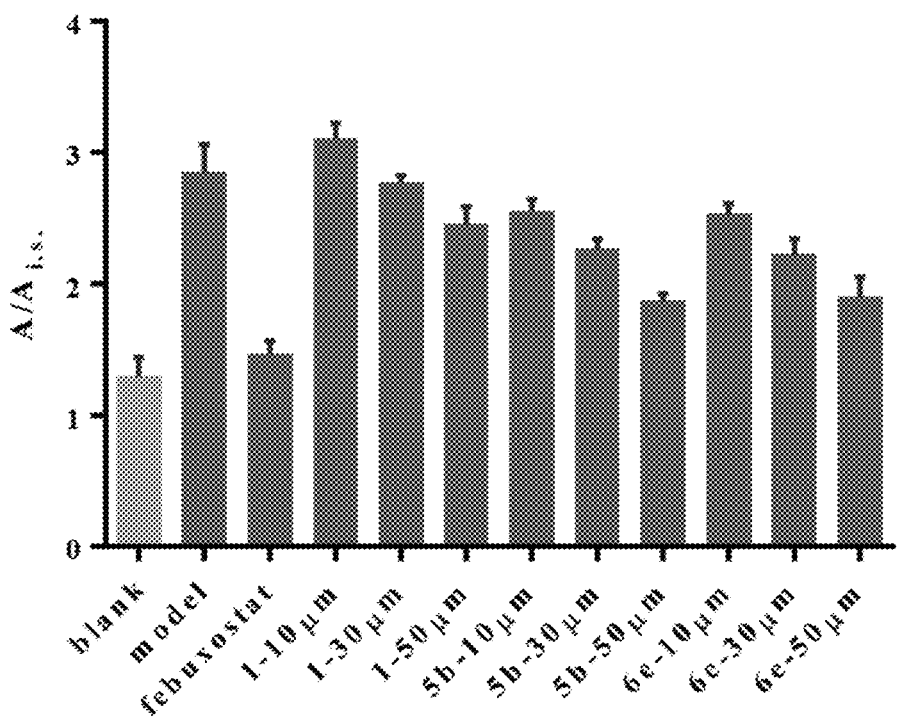
FIG. 2: Inhibitory effect of derivatives 5b and 6e and Salvianolic acid C (1) on uric acid in cells

The present invention will be further described in detail below with reference to the embodiments, but the embodiments of the present invention are not limited thereto.

The assay instrument used in this article:

American Agilent G1969 TOF/MS mass spectrometer is used for high resolution mass spectrometry;

Swiss Bruker AV-300 or 500 NMR is used for nuclear magnetic resonance;

The reagents are what was purchased from Sigma-Aldrich or Aladdin, and the reagents are of analytical grade or chemical purity, and the deuterated reagents are what was purchased from CIL Reagent, Cambridge, USA.

Embodiment 1

1. Synthesis of Aryl Benzofuran Amidated Derivatives 5a and 6a (1) Tournefolic Acid A Accurately weigh Salvianolic acid C (1) (245 mg, 0.498 mmol) into a two-neck round bottomed flask, add 20 mL of MeOH/H$_2$O (5:1 v/v), perform ultrasonic until the sample is completely dissolved, and add the inorganic base (NaOH or KOH) that is accurately weigh in the appropriate amount and continuously monitor the reaction by TLC (chloroform/methanol/formic acid 8:1:1 v/v/v) under heating until the material disappears completely. After the reaction is completed, the mixture is allowed to stand to cool to room temperature, and the solvent MeOH is evaporated, and then add 15 mL of distilled water for dilution, the mixture is then cooled with an ice bath, and add a 10% aqueous HCl solution by drops into with continuous stirring until pH is 3 to 4 and stop adding the drops. Add Ethyl acetate (20 mL×3) for extraction, and combine the organic layers, wash with saturated NaCl solution, dry it with MgSO$_4$, concentrate it under reduced pressure to obtain a crude product. Perform isocratic elution by silica gel column chromatography (chloroform/methanol/formic acid 10:1:0.1 v/v/v) to receive the product Tournefolic acid A (138 mg, yield 89%).

The structure of the reaction product obtained from experimental procedure (1) was analyzed.

Physical and chemical properties: Deep yellow powder (TLC R$_f$=0.42 chloroform/methanol/formic acid 8:1:1).

Spectrum information: $^1$H NMR (CD$_3$OD, 300 MHz) δ 7.92 (d, 1H, J=15.9 Hz), 7.41-7.29 (m, 3H), 7.18 (s, 1H), 6.88 (d, 1H, J=8.1 Hz), 6.73 (d, 1H, J=8.1 Hz), 6.43 (d, 1H, J=15.9 Hz); $^{13}$C NMR (CD$_3$OD, 75 MHz) δ 171.3, 159.3, 148.0, 146.7, 145.7, 144.6, 144.3, 132.5, 126.1, 123.4, 119.7, 118.7, 116.7, 116.0, 113.3, 111.7, 99.2. HR-MS (ESI) m/z: found 311.0563 [M−H]$^−$, calcd. for C$_{17}$H$_{12}$O$_6$ 311.0561.

According to the above spectrum information, the chemical formula of Tournefolic acid A was identified as C$_{17}$H$_{12}$O$_6$. The structure is as follows.

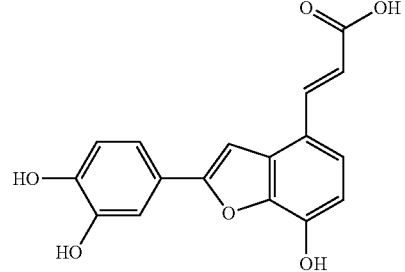 [SMILES: O=C(O)/C=C/c1ccc(O)c2oc(-c3ccc(O)c(O)c3)cc12]

(2) Methyl (S)-2-amino-3-(3,4-dihydroxyphenyl) propanoate Hydrochloride (4a)

Accurately measure 5 mL of anhydrous methanol into a round bottomed flask, cool in an ice bath for 15 min, slowly add SOCl$_2$ (493 μL, 6.780 mmol) by drops, and stir at 0° C. for 30 min, then add the accurately weighed L-DOPA (800 mg, 4.520 mmol), allow it to stand to cool to room temperature and stir for 24 h. After the reaction is completed, evaporate the solvent and react the remaining SOCl$_2$, use MeOH and Et$_2$O to wash the mixture alternatively three times, and evaporate it to dryness to obtain the product L-dopa methyl ester hydrochloride (1.03 g, yield 93%).

The structure of the reaction product obtained from experimental procedure (2) was analyzed.

Physical and chemical properties: White powder (TLC R$_f$=0.64, chloroform/methanol 10:1).

Spectrum information: $^1$H NMR (D$_2$O, 300 MHz) δ 6.78 (d, 1H, J=8.2 Hz), 6.78 (d, 1H, J=1.8 Hz), 6.68 (dd, 1H, J=1.8, 8.1 Hz), 4.35 (t, 1H, J=6.6 Hz), 3.82 (s, 3H), 3.18 (dd, 1H, J=5.9, 14.6 Hz), 3.06 (dd, 1H, J=7.7, 14.6 Hz). $^{13}$C NMR (D$_2$O, 75 MHz) δ 170.6, 144.8, 144.2, 126.6, 122.3, 117.4, 117.1, 54.8, 54.0, 35.4. ESI-MS m/z: 212.3 [M+H]$^+$.

According to the above spectrum information, the chemical formula of compound 4a was identified as $C_{10}H_{14}ClNO_4$. The structure is as follows.

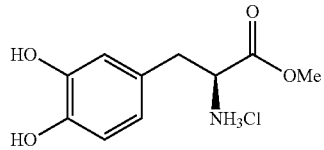

4a

(3) Methyl (S,E)-3-(3,4-dihydroxyphenyl)-2-(3-(2-(3,4-dihydroxyphenyl)-7-hydroxybenzofuran-4-yl)acrylamido)propanoate (5a)

Accurately weigh Thorneefolic acid A (36 mg, 0.115 mmol) into a round bottomed flask, add 4 mL of DMF/$CH_2Cl_2$ (4:1 v/v), perform ultrasonic dissolution and cooling in an ice bath, and then add accurately weighed EDCI (33.1 mg), 0.173 mmol) and HoBt (23.3 mg, 0.173 mmol); cool it in ice-bath for 10 min and keep stirring. Add accurately weighed L-dopa methyl ester hydrochloride (34.1 mg, 0.138 mmol) and $Et_3N$ (34.8 mg, 0.345 mmol), react in ice bath for 30 min, stir at room temperature, continuously monitor the reaction by TLC (chloroform/methanol/formic acid 8:1:1 v/v/v) until the material disappears. After the reaction is stopped, evaporate the solvent to dryness, and add 15 mL of distilled water to dilute the sample, cool it in an ice bath, and add a few drops of 10% aqueous HCl solution and shake it well. Extract it with Ethyl acetate (15 mL×4), combine the organic layers, let it concentrate under reduced pressure, and wash with saturated brine and dry it with $MgSO_4$. The sample mixture is separated and purified on a silica gel column (chloroform/methanol 15:1→10:1 v/v) to receive product 5a (29.6 mg, yield 51%).

The structure of the reaction product obtained from experimental procedure (3) was analyzed.

Physical and chemical properties: Deep yellow powder (TLC $R_f$=0.61, chloroform/methanol/formic acid 8:1:1).

Spectrum information: $^1H$ NMR ($CD_3OD$, 300 MHz) δ 7.74 (d, 1H, J=15.6 Hz), 7.39 (s, 1H), 7.34 (d, 1H, J=8.7 Hz), 7.28 (s, 1H), 6.87 (d, 1H, J=8.1 Hz), 6.74-6.63 (m, 4H), 6.55 (d, 1H, J=7.2 Hz), 4.76-4.72 (m, 1H), 3.72 (s, 3H), 3.11-3.00 (dd, 1H, J=13.5, 6.0 Hz), 2.99-2.89 (dd, 1H, J=13.5, 7.5 Hz); $^{13}C$ NMR ($CD_3OD$, 75 MHz) δ 173.8, 169.3, 159.1, 147.9, 146.8, 146.3, 145.3, 145.3, 144.5, 140.7, 132.0, 129.5, 126.0, 123.5, 121.7, 120.2, 118.6, 118.4, 117.3, 116.7, 116.4, 113.4, 111.6, 99.5, 55.8, 52.6, 38.2. HR-MS (ESI) m/z: found 504.1302 [M−H]$^-$, calcd. for $C_{27}H_{23}NO_9$ 504.1300.

According to the above spectrum information, the chemical formula of compound 5a was identified as $C_{27}H_{23}NO_9$. The structure is as follows.

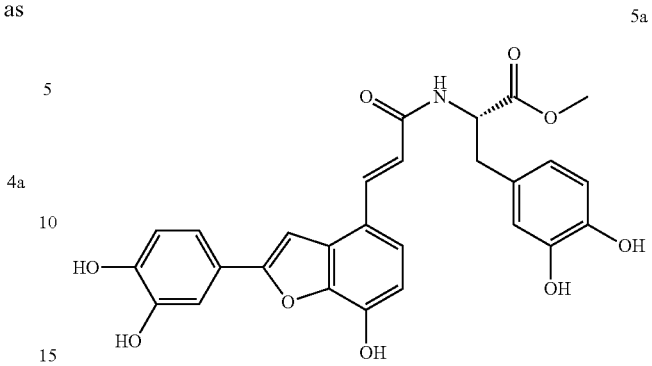

5a

(4) (S,E)-3-(3,4-dihydroxyphenyl)-2-(3-(2-(3,4-dihydroxyphenyl)-7-hydroxybenzofuran-4-yl)acrylamido)propanoic Acid (6a)

Accurately weigh compound 5a (18 mg, 0.036 mmol) into a two-necked flask, add 5 mL of MeOH/$H_2O$ (4:1 v/v) to dissolve the compound, then add NaOH (17.4 mg, 0.44 mmol), and warm it to reflux, monitor the reaction by TLC (chloroform/methanol/formic acid 8:1:1) until the reaction is complete. After the reaction is stopped, the reaction mixture is cooled in an ice bath, and 10% aqueous HCl solution is added by drops and stirred continuously until pH is 3 to 4, and the mixture is then evaporated to dryness, and then, 10 mL of distilled water before it is extracted with ethyl acetate (10 mL×4); combine the organic layers, concentrate it under reduced pressure and wash with brine and dry it with $MgSO_4$. The sample mixture is then separated by preparative liquid chromatography (Agilent zorbax-$C_{18}$, 5 μm, 20×250 mm) at a flow rate of 8 mL/min, a detection wavelength of 281 nm, and a mobile phase: acetonitrile-0.1% formic acid-water to obtain the target product 6a (11.6 mg, yield 66%).

The structure of the reaction product obtained from experimental procedure (1) was analyzed.

Physical and chemical properties: Yellow-green powder (TLC $R_f$=0.48, chloroform/methanol/formic acid 8:1:1).

Spectrum information: $^1H$ NMR (DMSO-$d_6$, 300 MHz) δ 8.15 (br s, 4H), 7.54 (d, 1H, J=15.9 Hz), 7.43 (s, 1H), 7.35 (s, 1H), 7.28 (d, 1H, J=8.1 Hz), 7.23 (d, 1H, J=8.4 Hz), 6.88 (d, 1H, J=8.1 Hz), 6.79-6.72 (q, 2H, J=15.9 Hz), 6.65-6.60 (m, 2H), 6.50 (d, 1H, J=8.1 Hz), 4.50 (m, 1H), 3.00-2.91 (d, 1H, J=14.1, 5.1 Hz), 2.84-2.74 (d, 1H, J=13.5, 8.7 Hz); $^{13}C$ NMR (DMSO-$d_6$, 75 MHz) δ 173.3, 165.6, 156.9, 146.9, 145.7, 145.0, 143.9, 143.8, 142.7, 137.8, 129.6, 128.3, 125.7, 121.1, 119.9, 119.2, 118.6, 117.0, 116.5, 116.1, 115.4, 112.4, 110.6, 99.0, 53.9, 36.7. HR-MS (ESI) m/z: found 492.1296 [M+H]$^+$, calcd. for $C_{26}H_{21}NO_9$ 492.1289.

According to the above spectrum information, the chemical formula of compound 6a was identified as $C_{26}H_{21}NO_9$. The structure is as follows.

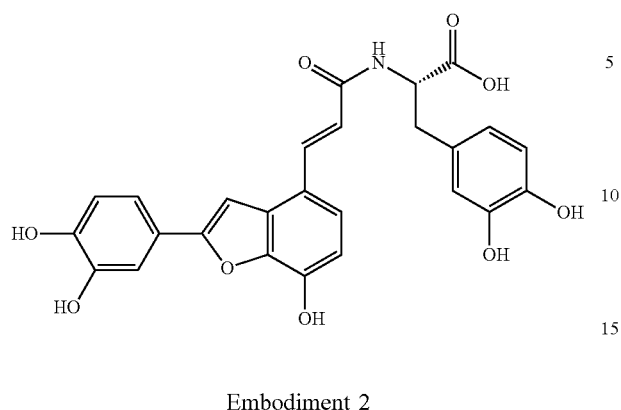

Embodiment 2

2. Synthesis of Aryl Benzofuran Amidated Derivatives 5b and 6b (1)-(2) are the same as the method for preparing an intermediate in the same manner as in Embodiment 1.

(3) Methyl (R,E)-3-(3,4-dihydroxyphenyl)-2-(3-(2-(3,4-dihydroxyphenyl))-7-Hydroxybenzofuran-4-yl) acrylamido)propanoate (5b)

Accurately weigh Thorneefolic acid A (32 mg, 0.103 mmol) into a round bottomed flask, add 3.5 mL of DMF/$CH_2C_2$ (5:1 v/v), perform ultrasonic until the sample is dissolved and cool it in an ice bath, and then add accurately weighed EDCI (31.6 mg, 0.165 mmol) and HoBt (22.3 mg, 0.165 mmol); cool it in ice-bath for 10 min and keep stirring. Add accurately weighed D-dopa methyl ester hydrochloride (30.5 mg, 0.124 mmol) and $Et_3N$ (31.2 mg, 0.309 mmol), react in ice bath for 30 min, stir at room temperature, continuously monitor the reaction by TLC (chloroform/methanol/formic acid 8:1:1) until the material disappears. After the reaction is stopped, evaporate the solvent to dryness, and add 15 mL of distilled water to dilute the sample, cool it in an ice bath, and add a few drops of 10% aqueous HCl solution and shake it well. Extract it with Ethyl acetate (15 mL×4), combine the organic layers, let it concentrate under reduced pressure, and wash with saturated brine and dry it with $MgSO_4$. The sample mixture is separated and purified on a silica gel column (chloroform/methanol 15:1→10:1 v/v) to receive product 5b (30 mg, yield 58%).

The structure of the reaction product obtained from experimental procedure (1) was analyzed.

Physical and chemical properties: Yellow green powder (TLC $R_f$=0.6, chloroform/methanol/formic acid 8:1:1).

Spectrum information: $^1H$ NMR ($CD_3OD$, 300 MHz) δ 7.74 (d, 1H, J=15.6 Hz), 7.39 (s, 1H), 7.37-7.32 (d, 1H, J=8.4 Hz), 7.29-7.24 (m, 2H), 6.87 (d, 1H, J=8.1 Hz), 6.73-6.65 (m, 4H), 6.55 (d, 1H, J=8.4 Hz), 5.08 (m, 1H), 4.06 (s, 3H), 4.00 (s, 3H), 3.94 (s, 3H), 3.77 (s, 3H), 3.23 (m, 1H), 2.93 (m, 1H); $^{13}C$ NMR ($CD_3OD$, 75 MHz) δ 172.4, 165.6, 157.0, 146.9, 145.7, 145.0, 144.5, 143.9, 142.7, 138.0, 129.7, 127.8, 125.7, 121.1, 119.8, 118.7, 118.4, 117.0, 116.4, 116.1, 115.4, 112.3, 110.6, 96.9, 54.0, 51.8, 36.7. HR-MS (ESI) m/z: found 504.1311 [M+H]$^+$, calcd. for $C_{27}H_{23}NO_9$ 504.1300.

According to the above spectrum information, the chemical formula of compound 5b was identified as $C_{27}H_{23}NO_9$. The structure is as follows.

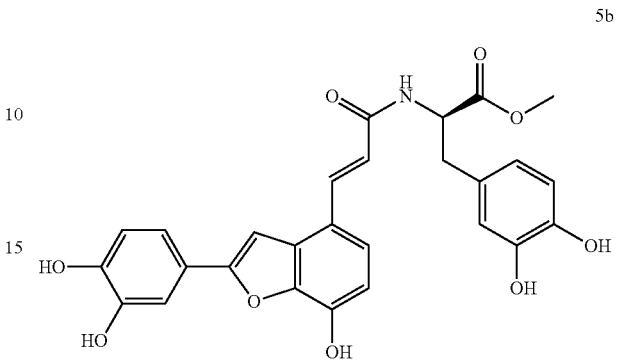

(4) (R,E)-3-(3,4-dihydroxyphenyl)-2-(3-(2-(3,4-dihydroxyphenyl)-7-hydroxybenzofuran-4-yl) acrylamido) propanoic Acid (6b)

Accurately weigh compound 5b (18 mg, 0.036 mmol) into a two-necked flask, add 5 mL of MeOH/$H_2O$ (3:1 v/v) to dissolve the compound, then add accurately weighed NaOH (17.1 mg, 0.428 mmol), and warm it to reflux, monitor the reaction by TLC (chloroform/methanol/formic acid 8:1:1) until the reaction is complete. After the reaction is stopped, ice cool the reaction mixture, add 10% HCl solution by drops and stir it to pH 3~4, evaporate it to dryness, add 10 mL of distilled water, and extract it with ethyl acetate (10 mL×4); combine the organic layers, let it concentrate, and wash with saturated brine and dry it with $MgSO_4$; then the mixture is separated by preparative liquid chromatography (Agilent zorbax-$C_{18}$, 5 μm, 20×250 mm), flow rate 8 mL/min, detection wavelength 281 nm, mobile phase: acetonitrile-0.1% formic acid-water gave product 6b (9.5 mg, yield 54%).

The structure of the reaction product obtained from experimental procedure (1) was analyzed.

Physical and chemical properties: Yellow powder (TLC $R_f$=0.46, chloroform/methanol/formic acid 8:1:1).

Spectrum information: $^1H$ NMR (DMSO-$d_6$, 300 MHz) δ 8.21 (br s, 4H), 7.53 (d, 1H, J=15.9 Hz), 7.43 (s, 1H), 7.35 (s, 1H), 7.23 (d, 1H, J=8.1 Hz), 7.22 (d, 1H, J=8.1 Hz), 6.87 (d, 1H, J=8.4 Hz), 6.80-6.70 (q, 2H, J=15.9 Hz), 6.65-6.59 (m, 2H), 6.43 (d, 1H, J=8.4 Hz), 4.50 (m, 1H), 2.98-2.91 (d, 1H, J=14.2, 4.9 Hz), 2.81-2.73 (d, 1H, J=14.2, 8.3 Hz); $^{13}C$ NMR (DMSO-$d_6$, 75 MHz) δ 173.6, 165.4, 156.9, 146.9, 145.7, 144.9, 143.8, 143.8, 142.7, 137.6, 129.5, 128.5, 125.7, 121.0, 119.9, 119.3, 118.6, 116.9, 116.6, 116.1, 115.3, 112.4, 110.5, 99.0, 54.2, 36.8. HR-MS (ESI) m/z: found 492.1293 [M+H]+, calcd. for $C_{26}H_{21}NO_9$ 492.1289.

According to the above information of high resolution mass spectrum and NMR spectrum, the chemical formula of compound 6b was identified as $C_{26}H_{21}NO_9$. The structure is as follows.

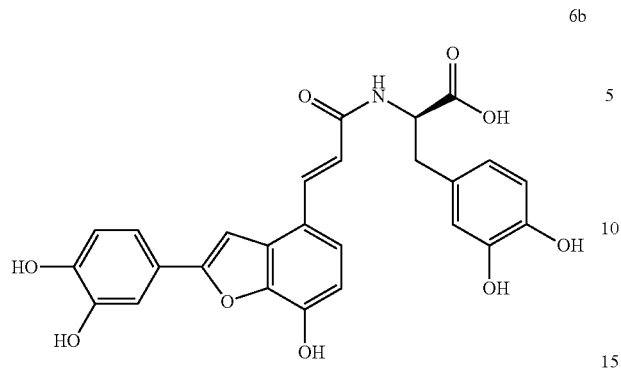

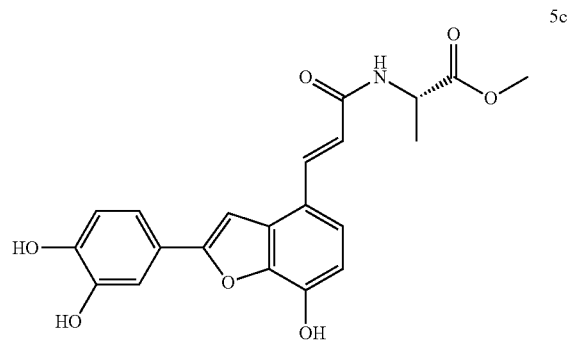 [SMILES: COC(=O)[C@H](C)NC(=O)/C=C/c1ccc(O)c2oc(-c3ccc(O)c(O)c3)cc12]

Embodiment 3

3. Synthesis of Aryl Benzofuran Amidated Derivatives 5c and 6c (1)-(2) are the same as the method for preparing an intermediate in the same manner as in Embodiment 1.

(3) Methyl (E)-(3-(2-(3,4-dihydroxyphenyl)-7-hydroxybenzofuran-4-yl)acryloyl)-L-alaninate (5c)

Accurately weigh Thorneefolic acid A (35 mg, 0.112 mmol) into a round bottomed flask, add 4 mL of DMF/$CH_2Cl_2$ (3:1 v/v), perform ultrasonic dissolution of the sample and cooling in an ice bath to 0° C.; and add EDCI (32.3 mg, 0.168 mmol) and HoBt (22.6 mg, 0.168 mmol); cool it in ice-bath for 10 min and keep stirring. Add accurately weighed L-Alanine methyl ester hydrochloride (18.7 mg, 0.134 mmol) and $Et_3N$ (33.9 mg, 0.336 mmol), react in ice bath for 30 min, stir at room temperature, continuously monitor the reaction by TLC (chloroform/methanol/formic acid 8:1:1) until the material disappears. After the reaction is stopped, evaporate the solvent to dryness, and add 15 mL of distilled water to dilute the sample, cool it in an ice bath, and add a few drops of 10% aqueous HCl solution and shake it well. Extract it with Ethyl acetate (15 mL×4), combine the organic layers, let it concentrate under reduced pressure, and wash with saturated brine and dry it with $MgSO_4$. The sample mixture is purified on a silica gel column (chloroform/methanol 20:1→8:1 v/v) to receive product 5c (28.4 mg, yield 64%).

The structure of the reaction product obtained from experimental procedure (3) was analyzed.

Physical and chemical properties: Light green powder (TLC $R_f$=0.65, chloroform/methanol/formic acid 8:1:1).

Spectrum information: $^1$H NMR (CD$_3$OD, 300 MHz) δ 7.77 (d, 1H, J=15.9 Hz), 7.39 (s, 1H), 7.35 (d, 1H, J=8.1 Hz), 7.32-7.25 (m, 2H), 6.87 (d, 1H, J=8.1 Hz), 6.75-6.70 (d, 1H, J=8.4 Hz), 6.70-6.63 (d, 1H, J=15.9 Hz), 4.62-4.53 (dd, 1H, J=14.7, 7.5 Hz), 3.75 (s, 3H), 1.46 (d, 3H, J=7.2 Hz); $^{13}$C NMR (CD$_3$OD, 75 MHz) δ 174.9, 169.2, 159.1, 148.0, 146.8, 145.4, 144.5, 140.7, 132.1, 125.9, 123.5, 120.2, 118.6, 118.4, 116.7, 113.4, 111.7, 99.5, 52.8, 49.7, 17.7. HR-MS (ESI) m/z: found 396.1089 [M−H]$^-$, calcd. for $C_{21}H_{19}NO_7$ 396.1089.

According to the above information of high resolution mass spectrum and NMR spectrum, the chemical formula of compound 5c was identified as $C_{21}H_9NO_7$. The structure is as follows.

(4) (E)-(3-(2-(3,4-dihydroxyphenyl)-7-hydroxybenzofuran-4-yl)acryloyl)-L-alanine (6c)

Accurately weigh compound 5c (19 mg, 0.048 mmol) into a two-necked flask, add 5 mL of MeOH/$H_2O$ (3:1 v/v) to dissolve the compound, then add NaOH (19.1 mg, 0.478 mmol), and warm it to reflux, monitor the reaction by TLC (chloroform/methanol/formic acid 8:1:1) until the reaction is complete. After the reaction is stopped, ice cool the reaction mixture, add 10% HCl solution by drops and stir it to pH 3~4, evaporate it to dryness, add 10 mL of distilled water, and extract it with ethyl acetate (10 mL×4); combine the organic layers, let it concentrate, and wash with saturated brine and dry it with $MgSO_4$; then the mixture is separated by preparative liquid chromatography (Agilent zorbax-$C_{18}$, 5 μm, 20×250 mm), flow rate 8 mL/min, detection wavelength 281 nm, mobile phase: acetonitrile-0.1% Formic acid-water gave product 6c (13.1 mg, yield 71%).

The structure of the reaction product obtained from experimental procedure (1) was analyzed.

Physical and chemical properties: Yellow green powder (TLC $R_f$=0.48, chloroform/methanol/formic acid 8:1:1).

Spectrum information: $^1$H NMR (CD$_3$OD, 300 MHz) δ 7.53 (d, 1H, 0.1=15.6 Hz), 7.44 (s, 1H), 7.36 (s, 1H), 7.32-7.20 (m, 2H), 6.83 (d, 1H, J=7.8 Hz), 6.82 (t, 2H, J=15.6 Hz), 4.38 (m, 1H), 1.35 (d, 3H, J=6.6 Hz); $^{13}$C NMR (CD$_3$OD, 75 MHz) δ 174.5, 165.5, 157.0, 147.0, 145.8, 143.9, 142.8, 137.8, 129.6, 125.8, 121.1, 119.3, 118.7, 117.0, 116.2, 112.4, 110.6, 99.0, 48.7, 17.8. HR-MS (ESI) m/z: found 382.0941 [M−H]$^-$, calcd. for $C_{20}H_{17}NO_7$ 382.0932.

According to the above spectrum information, the chemical formula of compound 6c was identified as $C_{20}H_{17}NO_7$. The structure is as follows.

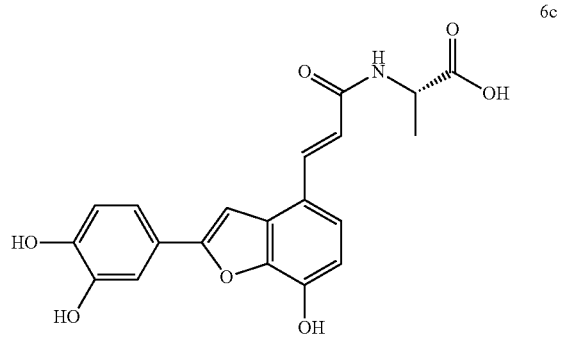 [SMILES: C[C@H](NC(=O)/C=C/c1ccc(O)c2oc(-c3ccc(O)c(O)c3)cc12)C(=O)O]

Embodiment 4

4. Synthesis of Aryl Benzofuran Amidated Derivatives 5d and 6d (1)-(2) are the same as the method for preparing an intermediate in the same manner as in Embodiment 1.

(3) Methyl (E)-(3-(2-(3,4-dihydroxyphenyl)-7-hydroxybenzofuran-4-yl)acryloyl)-L-phenylalaninate (5d)

Accurately weigh Thorneefolic acid A (35 mg, 0.112 mmol) into a 25 mL round bottomed flask, add 3 mL of DMF/CH$_2$Cl$_2$ (4:1 v/v), perform ultrasonic dissolution of the sample and cooling in an ice bath; and add EDCI (30.2 mg, 0.157 mmol) and HoBt (21.2 mg, 0.157 mmol); cool it in ice-bath for 10 min and keep stirring. Add L-phenylalanine methyl ester hydrochloride (28.9 mg, 0.134 mmol) and Et$_3$N (33.9 mg, 0.336 mmol), react in ice bath for 30 min, stir at room temperature, continuously monitor the reaction by TLC (chloroform/methanol/formic acid 8:1:1) until the material disappears. After the reaction is stopped, evaporate the solvent to dryness, and add 15 mL of distilled water to dilute the sample, cool it in an ice bath, and add a few drops of 10% aqueous HCl solution and shake it well. Extract it with Ethyl acetate (15 mL×3), combine the organic layers, let it concentrate, wash with saturated brine and dry it with MgSO$_4$; the sample mixture is then purified on a silica gel column (chloroform/methanol 20:1→10:1 v/v) to receive product 5d (24.3 mg, yield 46%).

The structure of the reaction product obtained from experimental procedure (1) was analyzed.

Physical and chemical properties: Yellow green powder (TLC R$_f$=0.69, chloroform/methanol/formic acid 8:1:1).

Spectrum information: $^1$H NMR (CD$_3$OD, 300 MHz) δ 7.73 (d, 1H, J=15.9 Hz), 7.39 (s, 1H), 7.34 (d, 1H, J=9.0 Hz), 7.31-7.18 (m, 7H), 6.87 (d, 1H, J=8.1 Hz), 6.71 (d, 1H, J=8.4 Hz), 6.65 (d, 1H, J=15.9 Hz), 4.95-4.86 (m, 1H), 3.72 (s, 3H), 3.27-3.17 (dd, 1H, J=13.5, 5.7 Hz), 3.12-3.01 (dd, 1H, J=13.5, 8.4 Hz); $^{13}$C NMR (CD$_3$OD, 75 MHz) δ 173.7, 169.3, 159.1, 148.0, 146.8, 145.3, 140.8, 138.2, 132.1, 130.2, 130.2, 129.5, 129.5, 127.9, 126.0, 123.5, 121.8, 120.2, 118.6, 118.3, 116.7, 113.4, 111.6, 99.5, 55.6, 52.7, 38.7. HR-MS (ESI) m/z: found 472.1414 [M−H]$^-$, calcd. for C$_{27}$H$_{23}$NO$_7$ 472.1402.

According to the above spectrum information, the chemical formula of compound 5d was identified as C$_{27}$H$_{23}$NO$_7$. The structure is as follows.

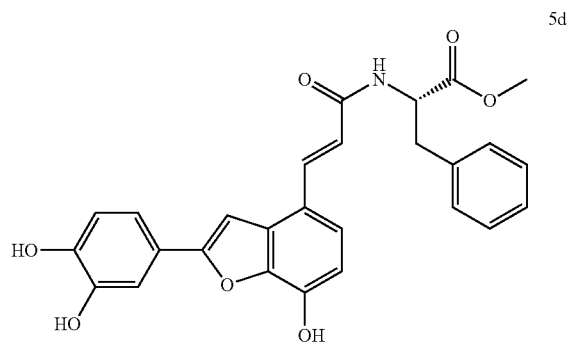 [SMILES: COC(=O)[C@H](Cc1ccccc1)NC(=O)/C=C/c1ccc(O)c2oc(-c3ccc(O)c(O)c3)cc12]

5d

(4) (E)-(3-(2-(3,4-dihydroxyphenyl)-7-hydroxybenzofuran-4-yl)acryloyl)-L-phenylalanine (6d)

Accurately weigh compound 5d (16 mg, 0.034 mmol) into a two-necked flask, add 5 mL of MeOH/H$_2$O (4:1 v/v) to dissolve the compound, then add NaOH (14.9 mg, 0.372 mmol), warm it to reflux, and monitor the reaction by TLC (chloroform/methanol/formic acid 8:1:1) until the reaction is complete. After the reaction is stopped, ice cool the reaction mixture, add 10% HCl solution by drops and stir it to pH 3~4, evaporate it to dryness, add 10 mL of distilled water, and extract it with ethyl acetate (10 mL×4); combine the organic layers, let it concentrate, and wash with saturated brine and dry it with MgSO$_4$; then the mixture is separated by preparative liquid chromatography (Agilent zorbax-C$_{18}$, 5 μm, 20×250 mm), flow rate 8 mL/min, detection wavelength 281 nm, mobile phase: acetonitrile-0.1% Formic acid-water gave product 6d (8.1 mg, yield 52%).

The structure of the reaction product obtained from experimental procedure (1) was analyzed.

Physical and chemical properties: Yellow green powder (TLC Rf=0.53, chloroform/methanol/formic acid 8:1:1).

Spectrum information: $^1$H NMR (DMSO-d$_6$, 300 MHz) δ 8.20 (br s, 2H), 7.54 (d, 1H, J=15.9 Hz), 7.42 (s, 1H), 7.35 (s, 1H), 7.30-7.20 (m, 7H), 6.88 (d, 1H, J=7.8 Hz), 6.79-6.69 (t, 2H, J=15.9 Hz), 4.63 (m, 1H), 3.16-3.08 (m, 1H), 3.01-2.91 (m, 1H); $^{13}$C NMR (DMSO-d$_6$, 75 MHz) δ 173.2, 165.5, 156.9, 146.9, 145.7, 143.8, 142.7, 137.73, 137.68, 129.6, 129.1, 129.1, 128.2, 128.2, 126.4, 125.6, 121.0, 119.0, 118.5, 116.9, 116.1, 112.4, 110.5, 96.9, 53.7, 37.2. HR-MS (ESI) m/z: found 458.1252 [M−H]$^-$, calcd. for C$_{26}$H$_{21}$NO$_7$ 458.1245.

According to the above spectrum information, the chemical formula of compound 6d was identified as C$_{26}$H$_{21}$NO$_7$. The structure is as follows.

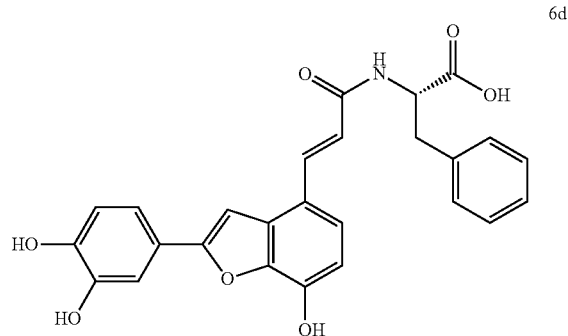 [SMILES: O=C(/C=C/c1ccc(O)c2oc(-c3ccc(O)c(O)c3)cc12)N[C@@H](Cc1ccccc1)C(=O)O]

6d

Embodiment 5

5. Synthesis of Aryl Benzofuran Amidated Derivatives 5e and 6e (1)-(2) are the same as the method for preparing an intermediate in the same manner as in Embodiment 1.

(3) Methyl (E)-(3-(2-(3,4-dihydroxyphenyl)-7-hydroxybenzofuran-4-yl)acryloyl)-L-tyrosinate (5e)

Accurately weigh Thorneefolic acid A (33 mg, 0.106 mmol) into a round bottomed flask, add 4 mL of DMF/CH$_2$C$_2$ (3:1 v/v), perform ultrasonic dissolution of the sample and cooling in an ice bath; and add EDCI (30.4 mg, 0.158 mmol) and HoBt (21.5 mg, 0.159 mmol); cool it in ice-bath for 10 min and keep stirring. Add L-tyrosine methyl ester hydrochloride (29.4 mg, 0.127 mmol) and Et$_3$N (32.1 mg, 0.318 mmol), react in ice bath for 30 min, stir at room temperature, continuously monitor the reaction by TLC (chloroform/methanol/formic acid 8:1:1) until the material disappears. After the reaction is stopped, evaporate the solvent to dryness, and dilute the sample with 15 mL of distilled water, cool it in an ice bath, then add 10% aqueous HCl solution by drops and shake it well. Extract it with Ethyl acetate (15 mL×4), combine the organic layers, let it concentrate under reduced pressure, and wash with saturated brine and dry it with MgSO$_4$. The sample mixture is then separated and purified on a silica gel column (chloroform/methanol 15:1→10:1 v/v) to obtain the derivative 5e (28.0 mg, yield 54%).

The structure of the reaction product obtained from experimental procedure (3) was analyzed.

Physical and chemical properties: Yellow green powder (TLC Rf=0.64, chloroform/methanol/formic acid 8:1:1).

Spectrum information: $^1$H NMR (CD$_3$OD, 300 MHz) δ 7.73 (d, 1H, J=16.2 Hz), 7.39 (s, 1H), 7.37-7.32 (d, 1H, J=8.1 Hz), 7.26 (s, 1H), 7.06 (d, 2H, J=8.4 Hz), 6.90-6.82 (m, 2H, J=7.5 Hz), 6.74-6.64 (m, 4H), 4.69-4.58 (m, 1H), 3.72 (s, 3H), 3.16-3.07 (dd, 1H, J=13.5, 6.0 Hz), 3.02-2.94 (dd, 1H, J=13.5, 8.1 Hz); $^{13}$C NMR (CD$_3$OD, 75 MHz) δ 174.5, 169.2, 159.3, 155.7, 147.3, 146.6, 145.2, 143.9, 141.7, 130.2, 130.2, 129.2, 124.3, 123.0, 122.0, 121.6, 120.2, 119.8, 116.9, 115.8, 115.8, 114.2, 108.4, 99.8, 56.2, 52.0, 38.2. HR-MS (ESI) m/z: found 488.1353 [M−H]$^-$, calcd. for C$_{27}$H$_{23}$NO$_8$ 488.1351.

According to the above spectrum information, the chemical formula of compound 5e was identified as C$_{17}$H$_{12}$O$_6$. The structure is as follows.

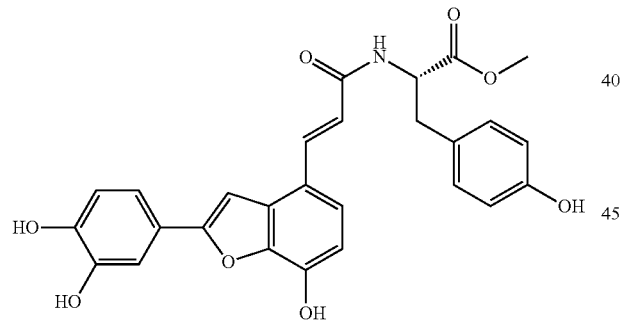

5e (4) (E)-(3-(2-(3,4-dihydroxyphenyl)-7-hydroxybenzofuran-4-yl)acryloyl)-L-tyrosine (6e)

Accurately weigh compound 6e (19 mg, 0.039 mmol) into a two-necked flask, add 5 mL of MeOH/H$_2$O (4:1 v/v) to dissolve the compound, then add NaOH (14.0 mg, 0,350 mmol), and warm it to reflux, monitor the reaction by TLC (chloroform/methanol/formic acid 8:1:1) until the reaction is complete. After the reaction is stopped, the reaction mixture is cooled in an ice bath, and 10% aqueous HCl solution is added by drops and stirred continuously until pH is 3 to 4, and the mixture is then evaporated to dryness, and then, 10 mL of distilled water before it is extracted with ethyl acetate (10 mL×4); combine the organic layers, concentrate it under reduced pressure and wash with brine and dry it with MgSO$_4$. The sample mixture is then separated by prepara-tive liquid chromatography (Agilent zorbax, SB-C$_{18}$, 5 μm, 20×250 mm) at a flow rate of 8 mL/min, a detection wavelength of 281 nm, and a mobile phase: acetonitrile-0.1% formic acid-water to obtain the reaction product 6e (11.8 mg, yield 62%).

The structure of the reaction product obtained from experimental procedure (1) was analyzed.

Physical and chemical properties: Yellow green powder (TLC Rf=0.5, chloroform/methanol/formic acid 8:1:1).

Spectrum information: $^1$H NMR (DMSO-d$_6$, 300 MHz) δ 7.95 (br s, 1H), 7.50 (d, 1H, J=16.2 Hz), 7.47 (s, 1H), 7.36 (s, 1H), 7.28 (d, 1H, J=8.1 Hz), 7.20 (d, 1H, J=8.1 Hz), 7.06-6.98 (m, 2H), 6.87 (d, 1H, J=8.1 Hz), 6.79 (d, 1H, J=16.2 Hz), 6.74 (d, 1H, J=8.1 Hz), 6.65-6.59 (m, 2H), 4.66 (m, 1H), 3.09-3.01 (q, 1H), 2.89-2.80 (q, 1H); $^{13}$C NMR (DMSO-d$_6$, 75 MHz) δ 174.3, 165.2, 156.9, 155.7, 147.0, 145.8, 143.8, 142.7, 137.3, 130.1, 130.1, 129.4, 128.4, 125.8, 121.0, 119.6, 118.6, 116.9, 116.2, 114.8, 114.8, 112.5, 112.5, 99.1, 54.8, 36.8. HR-MS (ESI) m/z: found 474.1201 [M−H]$^-$, calcd. for C$_{26}$H$_{21}$NO$_8$ 474.1194.

According to the above spectrum information, the chemical formula of compound 6e was identified as C$_{26}$H$_{21}$NO$_8$. The structure is as follows.

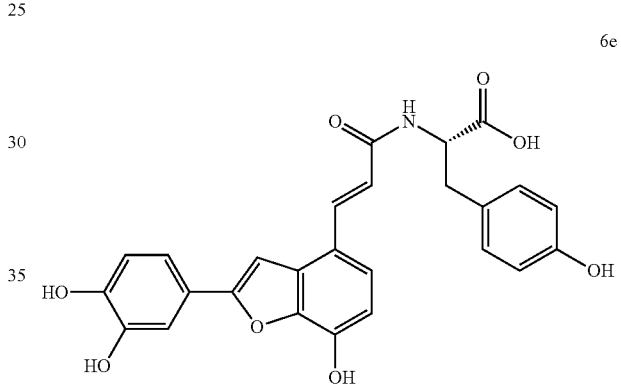

6e

Embodiment 6

6. Synthesis of Aryl Benzofuran Amidated Derivatives 5f and 6f (1)-(2) are the same as the method for preparing an intermediate in the same manner as in Embodiment 1.

(3) Methyl (E)-(3-(2-(3,4-dihydroxyphenyl)-7-hydroxybenzofuran-4-yl)acryloyl)-L-tryptophanate (5f)

Accurately weigh Thorneefolic acid A (41 mg, 0.131 mmol) into a round bottomed flask, add 5 mL of DMF/CH$_2$Cl$_2$ (5:1 v/v), perform ultrasonic dissolution of the sample and cooling in an ice bath to 0° C.; and add accurately weighed EDCI (37.8 mg, 0.197 mmol) and HoBt (26.5 mg, 0.196 mmol); cool it in ice-bath for 10 min and keep stirring. Add accurately weighed L-tryptophan methyl ester hydrochloride (39.9 mg, 0.157 mmol) and Et$_3$N (39.7 mg, 0.393 mmol), react in ice bath for 30 min, stir at room temperature, continuously monitor the reaction by TLC (chloroform/methanol/formic acid 8:1:1) until the material disappears. After the reaction is stopped, evaporate the solvent to dryness, and dilute the sample with 15 mL of distilled water, add 10% aqueous HCl solution by drops, cool it in an ice bath and shake it well. Extract it with Ethyl acetate (15 mL×4), combine the organic layers, let it concentrate under reduced pressure, and wash with saturated brine and dry it with MgSO$_4$. The sample mixture is then separated and purified on a silica gel column (chloroform/methanol 20:1→12:1 v/v) to obtain the derivative 5f (28.2 mg, yield 42%).

The structure of the reaction product obtained from experimental procedure (3) was analyzed.

Physical and chemical properties: Yellow green powder (TLC Rf=0.71, chloroform/methanol/formic acid 8:1:1).

Spectrum information: $^1$H NMR (CD$_3$OD, 300 MHz) δ 7.74 (d, 1H, J=15.6 Hz), 7.56 (d, 1H, J=7.5 Hz), 7.40-7.29 (m, 3H), 7.28-7.20 (m, 2H), 7.11 (s, 1H), 7.10-7.05 (d, 1H, J=7.5 Hz), 7.04-6.98 (t, 1H, J=7.5, 7.2 Hz), 6.86 (d, 1H, J=6.6 Hz), 6.75-6.69 (d, 1H, J=6.0 Hz), 6.69-6.62 (d, 1H, J=15.6 Hz), 4.95-4.89 (m, 1H), 3.69 (s, 3H), 3.43-3.35 (m, 1H), 3.29-3.20 (m, 1H); $^{13}$C NMR (CD$_3$OD, 75 MHz) δ 174.2, 169.4, 159.1, 148.2, 147.0, 145.9, 144.7, 140.8, 138.9, 138.1, 132.0, 128.8, 126.1, 124.4, 123.5, 122.5, 120.0, 119.9, 119.2, 118.6, 118.3, 117.3, 116.7, 113.4, 112.3, 111.8, 99.5, 55.2, 52.7, 28.8. HR-MS (ESI) m/z: found 511.1508 [M−H]$^−$, calcd. for C$_{29}$H$_{23}$N$_2$O$_7$ 511.1511.

According to the above spectrum information, the chemical formula of compound 5f was identified as C$_{29}$H$_{24}$N$_2$O$_7$. The structure is as follows.

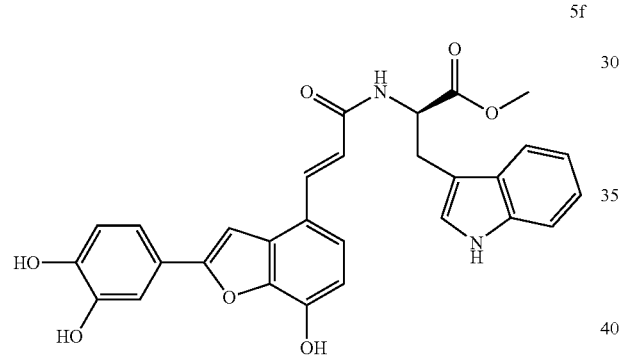

5f (4) (E)-(3-(2-(3,4-dihydroxyphenyl)-7-hydroxybenzofuran-4-yl)acryloyl)-D-tryptophan (6f)

Accurately weigh compound 5f (20 mg, 0.039 mmol) into a two-necked flask, add 5 mL of MeOH/H$_2$O (4:1 v/v) to dissolve the compound, then add NaOH (18.8 mg, 0.469 mmol), and warm it to reflux, monitor the reaction by TLC (chloroform/Methanol/formic acid 8:1:1) until the reaction is complete. After the reaction is stopped, the reaction mixture is cooled in an ice bath, and 10% HCl solution is added by drops and stirred continuously until pH is 3 to 4, and the mixture is then evaporated to dryness, and then, 10 mL of distilled water before it is extracted with ethyl acetate (10 mL×4); combine the organic layers, concentrate it and wash with brine and dry it with MgSO$_4$. The sample mixture is then separated by preparative liquid chromatography (Agilent zorbax-C$_{18}$, 5 μm, 20×250 mm) at a flow rate of 8 mL/min, a detection wavelength of 281 nm, and a mobile phase: acetonitrile-0.1% formic acid-water to obtain the reaction product 6f (10.7 mg, yield 55%).

The structure of the reaction product obtained from experimental procedure (1) was analyzed.

Physical and chemical properties: Yellow green powder (TLC Rf=0.58, chloroform/methanol/formic acid 8:1:1).

Spectrum information: $^1$H NMR (DMSO-d$_6$, 300 MHz) δ 10.85 (s, 1H), 8.17 (s, 1H), 7.62-7.56 (t, 2H, J=16.2 Hz), 7.44 (s, 1H), 7.37 (s, 1H), 7.34 (d, 1H, J=8.4 Hz), 7.29 (d, 1H, J=8.7 Hz), 7.24 (d, 1H, J=8.1 Hz), 7.18 (s, 1H), 7.09-7.03 (t, 1H, J=7.5 Hz), 7.01-6.96 (t, 1H, J=7.5 Hz), 6.89 (d, 1H, J=8.1 Hz), 6.80 (d, 1H, J=16.2 Hz), 6.75 (d, 1H, J=9.3 Hz), 4.72 (dd, 1H, J=12.8, 7.4 Hz), 3.69 (dd, 1H, J=14.4, 4.8 Hz), 3.29-3.20 (dd, 1H, J=14.4, 7.8 Hz); $^{13}$C NMR (DMSO-d$_6$, 75 MHz) δ 173.7, 165.7, 157.0, 147.0, 145.8, 143.9, 142.8, 137.9, 136.2, 129.6, 127.4, 125.9, 123.6, 121.1, 121.0, 119.3, 118.7, 118.5, 118.4, 117.0, 116.2, 112.4, 111.5, 110.6, 110.0, 99.1, 53.2, 27.6. HR-MS (ESI) m/z: found 497.1368 [M−H]$^−$, calcd. for C$_{28}$H$_{22}$N$_2$O$_7$ 497.1354.

According to the above spectrum information, the chemical formula of compound 6f was identified as C$_{28}$H$_{22}$N$_2$O$_7$. The structure is as follows.

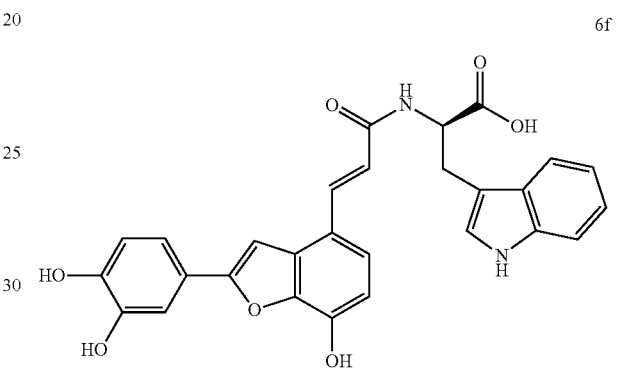

6f

Embodiment 7

7. Synthesis of Aryl Benzofuran Amidated Derivative 7

(2R)-3-(3,4-dimethoxyphenyl)-1-methoxy-1-oxopropan-2-yl (2E)-3-[2-(3,4-dimethoxyphenyl)-7-methoxy-1-benzofuran-4-yl]prop-2-enoate (7)

Accurately weigh Salvianolic acid C (206 mg, 0.419 mmol) into a round bottomed two-necked flask, add 15 mL of Me$_2$CO to dissolve it ultrasonically, accurately weigh (measure) K$_2$CO$_3$ (1.16 g, 8.374 mmol), Me$_2$SO$_4$ (714.5 mL, 7.542 mmol) and add them into the salvianolic acid C sample solution, perform refluxed reaction, and monitor it by TLC (cyclohexane/ethyl acetate 1:1) until the starting material is disappeared. After the reaction is stopped, evaporate solvent until it is dry, dilute with 10% saturated aqueous NH$_4$Cl solution (20 mL) and extract with Ethyl acetate (20 mL×4); combine the organic layers, wash with brine and dry it with MgSO$_4$; concentrate it under reduced pressure to obtain the compound sample. Elute with a silica gel column gradient (hexane/ethyl acetate: 10:1, 5:1 v/v) to afford product 7 (431 mg, yield 92%).

The structure of the reaction product obtained from experimental procedure (1) was analyzed.

Physical and chemical properties: Yellow powder (TLC Rf=0.62, cyclohexane/ethyl acetate 1:1).

Spectrum information: $^1$H NMR (CDCl$_3$, 300 MHz) δ 7.96 (d, 1H, J=15.9 Hz), 7.53 (dd, 1H, J=8.4, 2.1 Hz), 7.39 (m, 2H), 7.17 (s, 1H), 6.97 (d, 1H, J=8.4 Hz), 6.82 (m, 4H), 6.50 (d, 1H, J=15.9 Hz), 5.41 (q, 1H, J=13.2, 7.5, 5.4 Hz), 4.09 (s, 3H), 4.03 (s, 3H), 3.96 (s, 3H), 3.88 (s, 3H), 3.86 (s, 3H), 3.78 (s, 3H), 3.21 (dd, 2H, J=5.1, 2.1 Hz); $^{13}$C NMR (CDCl$_3$, 75 MHz) δ 170.5, 166.7, 157.6, 150.1, 149.2, 148.8, 148.8, 146.9, 144.1, 143.7, 130.7, 128.4, 125.8, 122.7, 121.4, 121.4, 118.5, 114.9, 112.5, 111.3, 111.2, 108.2, 106.6, 99.2, 73.1, 56.2, 56.2, 56.0, 55.8, 55.8, 52.4, 37.2. HR-MS (ESI) m/z: found 577.2068 [M+H]$^+$, calcd. for C$_{32}$H$_{33}$O$_{10}$ 577.2079.

According to the above spectrum information, the chemical formula of compound 7 was identified as C$_{32}$H$_{32}$O$_{10}$. The structure is as follows.

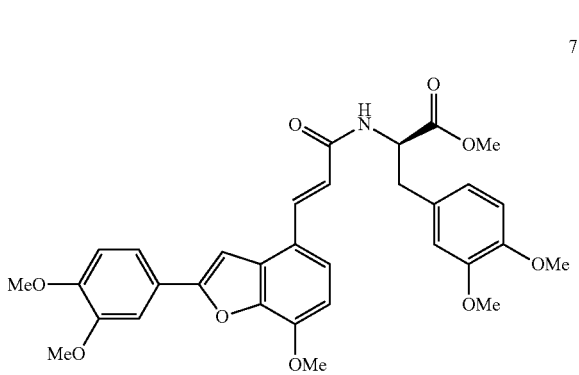

7

Embodiment 8

8. Synthesis of Aryl Benzofuran Amidated Derivative 9a

Methyl (S,E)-3-(3,4-dihydroxyphenyl)-2-(3-(2-(3,4-dimethoxyphenyl)-7-methoxybenzofuran-4-yl)acrylamido)propanoate (9a)

Accurately weigh reaction intermediate into a round bottomed flask, add 5 mL of DMF/CH$_2$Cl$_2$ (v/v 2:5), perform ultrasonic dissolution of the sample and cooling in an ice bath to 0° C.; and add EDCI (27.4 mg, 0.143 mmol) and HoBt (19.3 mg, 0.143 mmol); cool it in ice-bath for 10 min and keep stirring. Add L-Alanine methyl ester hydrochloride (30.3 mg, 0.169 mmol) and Et$_3$N (36.1 mg, 0.357 mmol), react in ice bath for 30 min, stir at room temperature, continuously monitor the reaction by TLC (cyclohexane/ethyl acetate 5:2) until the material disappears. After the reaction is stopped, evaporate the solvent to dryness, add 15 mL of distilled water to dilute the sample, and add a few drops of 10% aqueous HCl solution and shake it well. Extract it with Ethyl acetate (15 mL×3) to obtain the organic layers, concentrate it, wash with saturated aqueous solution of NaHCO$_3$ and saturated brine and dry it with MgSO$_4$ to obtain the compound sample. Perform elution with silica gel column chromatography (chloroform/methanol 80:1) to receive the reaction product 9a (37.7 mg, yield 52%).

The structure of the reaction product obtained from experimental procedure (1) was analyzed.

Physical and chemical properties: Yellow green powder (TLC Rf=0.57, cyclohexane/ethyl acetate 5:2).

Spectrum information: $^1$H NMR (CD$_3$OD, 300 MHz) δ 7.71 (d, 1H, J=15.6 Hz), 7.46 (d, 1H, J=8.7 Hz), 7.42 (s, 1H), 7.37-7.26 (d, 2H, J=8.4 Hz), 7.01 (d, 1H, J=7.8 Hz), 6.83 (d, 1H, J=8.1 Hz), 6.73-6.65 (t, 3H, J=15.6 Hz), 6.56 (d, 1H, J=8.1 Hz), 4.77-4.60 (dd, 1H, J=14.4, 7.8 Hz), 4.02 (s, 3H), 3.92 (s, 3H), 3.87 (s, 3H), 3.72 (s, 3H), 3.13-3.01 (dd, 1H, J=13.2, 5.4 Hz), 2.99-2.91 (dd, 1H, J=13.2, 7.8 Hz); $^{13}$C NMR (CD$_3$OD, 75 MHz) δ 173.8, 169.0, 158.5, 151.5, 150.8, 147.8, 146.3, 145.4, 140.5, 131.4, 129.5, 126.2, 124.4, 122.7, 121.7, 121.6, 119.54, 119.49, 117.3, 116.4, 113.2, 109.8, 107.9, 100.3, 56.71, 56.67, 56.5, 55.8, 52.7, 38.2. HR-MS (ESI) m/z: found 546.1777 [M−H]$^−$, calcd. for C$_{30}$H$_{28}$NO$_9$ 546.1770.

According to the above spectrum information, the chemical formula of compound 9a was identified as C$_{30}$H$_{29}$NO$_9$. The structure is as follows.

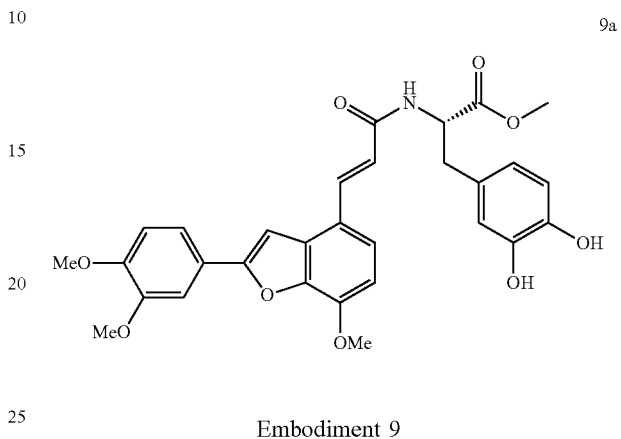

9a

Embodiment 9

9. Synthesis of Aryl Benzofuran Amidated Derivative 10a (S,E)-3-(3,4-dihydroxyphenyl)-2-(3-(2-(3,4-dimethoxyphenyl)-7-methoxybenzofuran-4-yl)acrylamido)propanoic Acid (10a)

Accurately weigh compound 9a (20 mg, 0.039 mmol) into a two-necked flask, add 5 mL of MeOH/H$_2$O (4:1 v/v) to dissolve the compound, then add NaOH (18.8 mg, 0.469 mmol), and warm it to reflux, monitor the reaction by TLC (cyclohexane/ethyl acetate/formic acid 2:1:0.1% v/v/v) until the reaction is complete. After the reaction is stopped, the reaction mixture is cooled in an ice bath, and 10% HCl solution is added by drops and stirred continuously until pH is 3 to 4, and the mixture is then evaporated to dryness, and then, 10 mL of distilled water before it is extracted with ethyl acetate (10 mL×4); combine the organic layers, concentrate it and wash with brine and dry it with MgSO$_4$. The sample mixture is then separated by preparative liquid chromatography (Agilent zorbax-C$_{18}$, 5 μm, 20×250 mm) at a flow rate of 8 mL/min, a detection wavelength of 281 nm, and a mobile phase: acetonitrile-0.1% formic acid-water to obtain the reaction product 10a (10.7 mg, yield 55%).

The structure of the reaction product obtained from experimental procedure (1) was analyzed.

Physical and chemical properties: Yellow green powder (TLC Rf=0.36, cyclohexane/ethyl acetate/formic acid 4:1: 0.1%).

Spectrum information: $^1$H NMR (DMSO-d$_6$, 300 MHz) δ 8.20-8.09 (t, 1H, 0.1=7.8 Hz), 7.68 (s, 1H), 7.62 (d, 1H, J=15.9 Hz), 7.55-7.45 (m, 2H), 7.41 (d, 1H, J=8.7 Hz), 7.11 (d, 1H, J=8.1 Hz), 6.98 (d, 1H, J=8.4 Hz), 6.82 (d, 1H, J=15.9 Hz), 6.67-6.58 (m, 2H), 6.49 (d, 1H, J=7.8 Hz), 4.58-4.46 (dd, 1H, J=13.6, 7.4 Hz), 4.01 (s, 3H), 3.89 (s, 3H), 3.83 (s, 3H), 3.00-2.92 (dd, 1H, J=14.1, 4.8 Hz), 2.83-2.75 (dd, 1H, J=13.6, 7.4 Hz); $^{13}$C NMR (DMSO-d$_6$, 75 MHz) δ 173.4, 165.2, 156.5, 149.9, 149.2, 145.7, 144.9, 143.9, 143.0, 136.8, 129.5, 128.4, 124.6, 122.2, 120.6, 120.3, 119.9, 117.9, 116.6, 115.3, 112.1, 108.4, 107.2, 100.0, 56.0, 55.8, 55.7, 54.2, 36.7. HR-MS (ESI) m/z: found 532.1620 [M−H]⁻, calcd. for $C_{29}H_{27}NO_9$ 532.1613.

According to the above spectrum information, the chemical formula of compound 10a was identified as $C_{29}H_{27}NO_9$. The structure is as follows.

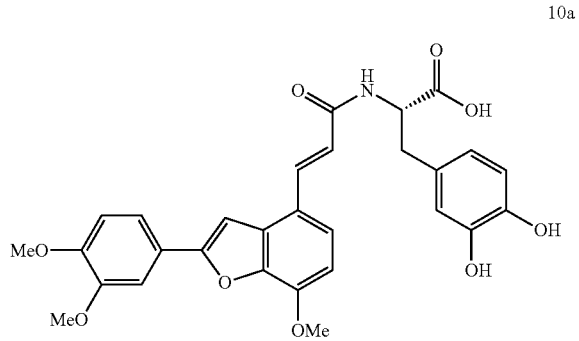 [SMILES: COc1ccc(-c2cc3c(/C=C/C(=O)N[C@@H](Cc4ccc(O)c(O)c4)C(=O)O)ccc(OC)c3o2)cc1OC]

10a

Embodiment 10

10. Synthesis of Aryl Benzofuran Amidated Derivative 9b

Methyl (R,E)-3-(3,4-dihydroxyphenyl)-2-(3-(2-(3,4-dimethoxyphenyl)-7-methoxybenzofuran-4-yl)acrylamido)propanoate (9b)

Accurately weigh reaction intermediate into a round bottomed flask, add 5 mL of DMF/CH₂Cl₂ (v/v 2:5), perform ultrasonic dissolution of the sample and cooling in an ice bath to 0° C.; and add EDCI (31.4 mg, 0.152 mmol) and HoBt (26.3 mg, 0.167 mmol); cool it in ice-bath for 10 min and keep stirring. Add D-Alanine methyl ester hydrochloride (37 mg, 0.181 mmol) and Et₃N (39 mg, 0.371 mmol) with N₂ protection, react in ice bath for 30 min, stir at room temperature, continuously monitor the reaction by TLC (cyclohexane/ethyl acetate 5:2 v/v) until the material disappears. After the reaction is complete, evaporate the solvent to dryness, add 15 mL of distilled water to dilute the sample, and add a few drops of 10% aqueous HCl solution and shake it well. Extract it with Ethyl acetate (15 mL×3) to obtain the organic layers, concentrate it, wash with saturated aqueous solution of NaHCO₃ and saturated brine and dry it with MgSO₄ to obtain the compound sample. Perform elution with silica gel column chromatography (cyclohexane/ethyl acetate 12:1) afforded the reaction product 9b (45.7 mg, yield 66%).

The structure of the reaction product obtained from experimental procedure (1) was analyzed.

Physical and chemical properties: Yellow green powder (TLC Rf=0.56, cyclohexane/ethyl acetate 5:2).

Spectrum information: ¹H NMR (CDCl₃, 300 MHz) δ 7.61 (d, 1H, J=15.3 Hz), 7.46-7.39 (m, 1H), 7.37-7.28 (m, 2H), 7.12 (d, 1H, 0.1=8.1 Hz), 6.93-6.89 (m, 2H), 6.65-6.60 (d, 2H, J=8.1 Hz), 6.53-6.48 (d, 1H, J=8.4 Hz), 6.28 (d, 1H, J=15.3 Hz), 5.02-4.90 (dd, 1H, J=13.8, 4.8 Hz), 3.97 (s, 3H), 3.91 (s, 3H), 3.74 (s, 3H), 3.49 (s, 3H), 3.24-3.11 (dd, 1H, J=14.4, 5.4 Hz), 3.09-2.95 (dd, 1H, J, =14.4, 4.8 Hz); ¹³C NMR (CDCl₃, 75 MHz) δ 172.5, 167.2, 157.3, 150.0, 149.3, 146.5, 144.4, 143.9, 140.1, 136.0, 130.9, 127.9, 124.1, 122.9, 121.2, 119.8, 118.6, 117.3, 116.3, 115.4, 111.4, 108.4, 106.6, 99.0, 56.3, 56.2, 56.1, 54.0, 52.6, 37.3. HR-MS (ESI) m/z: found 546.1777 [M−H]⁻, calcd. for $C_{30}H_{29}NO_9$ 546.1770.

According to the above spectrum information, the chemical formula of compound 9b was identified as $C_{30}H_{29}NO_9$. The structure is as follows.

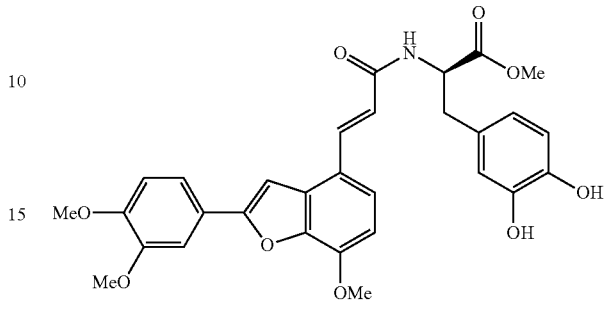

9b

Embodiment 11

Determination of Xanthine Oxidase Inhibitory Activity of Aryl Benzofuran Amidated Derivatives and Reagents (Amino Derivatives)

11.1 Preparation of Reagents and Standard Solutions (1) 75 mM phosphate buffer (PB, pH 7.4): containing KH₂PO₄ 0.0956 g, K₂HPO₄ 0.6946 g, EDTA 1.862 mg, dilute to 50 mL with pure water, to be used to dilute samples and other reagents;

(2) XOD solution: Take 25 U/2.6 mL of XOD, dilute to 0.08 U/mL of XOD working solution with 75 mM PB solution, mix well with a pipette, store on ice for future use;

(3) Substrate preparation: accurately weigh the appropriate amount of xanthine (XA) into 5 mL of 0.1 N NaOH solution, dissolve it ultrasonically, and add 95 mL of 75 mM PB solution to prepare a substrate mother liquor with a final concentration of 0.48 mM, perform vortex mixing for 1 min; it is to be freshly prepared before each experiment;

(4) Preparation of the test drug: accurately weigh the appropriate amount of the test drug, dissolve it in DMSO to prepare a 10 mM stock solution, and store at −20° C. in the dark. Use DB to dilute to different concentrations (0-100 mM) before the experiment, and the DMSO content is less than 0.1%.

11.2 Steps (1) Add 100 μL of different concentrations of the sample solution to be tested onto a 96-well plate, add 0.08 U/mL XOD 50 μL, and use the same volume of PB as a blank control and allopurinol as a positive control; incubate for 3 min at 37° C. on a microplate reader, and set up 4 replicate wells in parallel for each group.

(2) Add the substrate 0.48 mM XA 50 μL to start the reaction, read every 15 s at a wavelength of 295 nm and record the absorbance for a total of 7 min. Data processing: Data is processed by using Excel analysis and half-inhibitory concentration ($IC_{50}$) is calculated by using GraphPad Prism 6.0.2.

(3) Measurement results are shown in Table 1, which indicate that most of the synthesized benzofuran amidated derivatives have significantly xanthine oxidase inhibitory activity.

TABLE 1

Inhibitory activity of benzofuran amidated derivatives on xanthine oxidase

| Compound | IC$_{50}$ (μM) [a] | Compound | IC$_{50}$ (μM) |
|---|---|---|---|
| Allopurinol[b] | 2.31 | Salvianolic acid C | 8.26 |
| 5a | 9.88 | 6a | 4.81 |
| 5b | 3.99 | 6b | 12.12 |
| 5c | 10.8 | 6c | 6.36 |
| 5d | 14.91 | 6d | 6.04 |
| 5e | 13.48 | 6e | 4.51 |
| 5f | 31.72 | 6f | 4.98 |
| 7 | >60 | 9a | >60 |
| 9b | >60 | 10a | >60 |
| L-dopa | >60 | D-dopa | >60 |
| L-phe | >60 | L-ala | >60 |
| L-trp | >60 | L-tyr | >60 |
| L-cys | >60 | L-met | >60 |

[a] IC$_{50}$ value is the average of four parallel experiments;
[b] Reported in the literature: IC$_{50}$ = 2.55 μM;

Embodiment 12

The antioxidant activity of the synthesized benzofuran amidated derivative is evaluated by DPPH free radical scavenging experiment.

12.1 Preparation of Reagents and Standard Solutions (1) Preparation of DPPH solution: accurately weigh the appropriate amount of DPPH, add MeOH and perform ultrasonic dissolution to prepare 10 mM stock solution, and store at −20° C. Dilute to 0.1 mM with MeOH before the experiment and store in the dark;

(2) Preparation of the test drug: accurately weigh the appropriate amount of the test drug, dissolve it in MeOH to prepare a 10 m stock solution, and store at −20° C. in the dark. Use MeOH to dilute to different concentrations (0-100 mM) before the experiment.

12.2 Steps (1) Add 100 μL of different concentrations of the sample solution to be tested onto a 96-well plate, add 100 μL of 0.1 mM DPPH, and use the same volume of MeOH as a blank control and Quercetin as a positive control; After shaking for 1 min at 37° C. on a microplate reader, place it in the dark for 30 min, and set up 3 replicate wells in parallel.

(2) The absorbance is recorded with a microplate reader at a wavelength of 517 nm. Data processing: Data is processed by using Excel analysis and half-inhibitory concentration (IC$_{50}$) is calculated by using GraphPad Prism 6.0.2.

(3) As shown in Table 2, most of the aryl benzofuran derivatives have obvious antioxidant effects, and based on their structure it can be inferred that the phenolic hydroxy groups have an important influence on their ability to scavenge free radicals.

TABLE 2

Antioxidant activity of benzofuran amidated derivatives

| Compound | IC$_{50}$ (μM)[a] | Compound | IC$_{50}$ (μM) [a] |
|---|---|---|---|
| Quercetin[b] | 6.0 | Salvianolic acid C | 6.87 |
| 5a | 8.79 | 6a | 4.52 |
| 5b | 3.9 | 6b | 5.61 |
| 5c | 11.95 | 6c | 3.27 |
| 5d | 8.66 | 6d | 4.2 |
| 5e | 47.25 | 6e | 6.47 |
| 5f | 12.37 | 6f | 3.86 |
| 7 | >100 | 9a | 14.52 |
| 9b | 19.04 | 10a | 17.19 |

[a] IC$_{50}$ value is the average of three parallel experiments;
[b] Reported in the literature: IC$_{50}$ = 9.1 μM;

Embodiment 13

The antioxidant activity (the ability to scavenge superoxide anion) of the synthesized benzofuran amidated derivative is evaluated by a cell model.

After phagocytosis of bacteria, senescent denatured cells, immune complexes or oxidized low-density lipoproteins, mammalian macrophages cells enter a functional activation state, with enhanced intracellular lysosomal function and increased ROS levels, and they secrete and synthesize inflammatory cytokines. Lipopolysaccharide (LPS) is the main component of the cell wall of Gram-negative bacteria and is the main material basis for its pathogenesis; it can stimulate the production of monocytes/macrophages and release a large amount of reactive oxygen species (mainly including $O_2^-$ and $H_2O_2$), inflammatory factors such as nitric oxide (NO), IL-1β and Tumor necrosis factor-α (TNF-α) that are involved in the acute phase response of the body, causing inflammatory damage to the body. The present invention utilizes the LPS-stimulated macrophage model to evaluate the antioxidant activity of benzofuran amidated derivatives to scavenge superoxide anion at the cellular level.

13.1 Preparation of Reagents and Standard Solutions (1) Preparation of the test drug: accurately weigh the appropriate amount of the test drug, dissolve it in DMSO to prepare a 10 mM stock solution, and store at −20° C. in the dark.

(2) LPS: accurately weigh the appropriate amount of LPS, and prepare a sample stock solution of 0.1 g/ml, with DMEM and store at −20° C. for later use.

(3) Probe Stabilizer DTPA: Weigh accurately the amount of DTPA, prepare a 20 mM sample stock solution with DMSO, dilute to 100 M with PB, and store at 4° C. for use.

(4) HE: Prepare a 20 mmol/L stock solution by dissolving the probe with dimethyl sulfoxide under anaerobic and dark conditions, and store at −80° C. in the dark. Take it out before use, prepare a 10 μmol/L solution with DMEM, place it on ice and store it in the dark.

13.2 Steps

LPS stimulated macrophage RAW 264.7 modeling and administration:

(1) RAW 264.7 cells are cultured in Petri dishes (60 mm), 4 mL per dish, and incubated in a 5% $CO_2$ incubator with saturated humidity at 37° C. The experiment is divided into blank group, model group and drug-administered group. The model group and the drug-administered group are respectively added with the modeling agent LPS (prepared with DMEM) and the optimal LPS concentration is 0.1 μg/mL, while the modeling time is 24 h; take vitamin E as a positive control.

(2) After 12 h of cell culture, the supernatant is discarded, and the test drug with a final concentration of 10 μM containing 0.1 μg/mL LPS medium is added, and two parallel holes are provided for each sample to be tested.

(3) Continue to culture in a cell culture incubator for 24 h, the supernatant is discarded, the cells are washed with PBS, and added to DMEM medium containing the probe HE (10 μM) and cultured in the dark for 30 min.

(4) The cells are then washed twice with ice-cold PBS/ (100 μM) DTPA, then added 1 mL PBS/(100 μM) DTPA, before the cells are divided into two with a spatula (700 μL and 300 μL) and collected into EP tubes; then they are centrifuged at 13,000 rpm for 10 min at 4° C., the supernatant is removed, and the cell pellet are stored at −80° C. for future use. The first one contains 700 μL cell solution for the determination of LC-MS content of the test substance 2-OH-$E^+$, while the second one contains 300 μL cell solution for the determination of cell protein concentration.

13.3 LC-MS Analysis Conditions, Sample Pretreatment and Data Processing Methods (1) LC-MS chromatographic conditions: instrument: Agilent 1100 series LC-QMS; column: Agilent Zorbax SB-Aq (4.6×50 mm, 1.8 μm); mobile phase: 0.1% formic acid-water (phase A); 0.1% formic acid-acetonitrile (B); gradient conditions: 0~2 min, 5%~30% B; 2~5 min, 30% B; 5~7 min, 30%~100% B; 7~10 min, 100% B; flow rate: 1 mL/min; MS condition: positive ion mode, SIM (SIM1: 1.2~3 min $[M+H]^+288$ (galantamine); 3~10 min $[M]^+330$ (2-OH-$E^+$)); cracking voltage: 120 V; nitrogen flow rate: 10.0 L/min;

(2) Pretreatment of the sample to be tested: 500 μL acetonitrile is added to each EP tube, protected from light, sonicated (10 s, eight cycles, 100 W), and centrifuged at 12,000 g for 10 min at 4° C. The supernatant is transferred to a 1.5 mL EP tube and dried under vacuum for 1 h to obtain a red dried material; the sample is then re-dissolved with 100 μL of mass spectrometry water, and the internal standard substance galantamine is added to make the final concentration of the sample to be tested at 0.1 μM. The sample to be tested is then centrifuged at 13,000 rpm for 10 min at 4° C. and analyzed by LC-MS.

(3) Calculation of superoxide anion clearance rate: The amount of product 2-OH-E produced is evaluated by peak area/protein concentration. The compound's XOD inhibition rate or $O_2^-$. scavenging rate of is calculated by the following formula: $O_2^-$. free radical scavenging rate=$[A_{blank}-A_{sample}]/A_{blank} \times 100\%$, where $A_{blank}$ is the peak area value/protein concentration of the control group 2-OH-$E^+$; $A_{sample}$ is the peak area value/protein concentration of the sample group 2-OH-$E^+$.

13.4 Analysis of data results: The results are shown in Table 3. The 2-aryl benzofuran amidated derivatives 5a, 5b, 5c, 6b, 6c, 6d, 6e and Salvianolic acid C have obvious scavenging effect on superoxide anion produced by LPS-stimulated macrophage RAW 264.7 when compared to the model group. The derivatives 5a, 5b, 5c, 6b, 6d and 6e have exhibited better superoxide anion scavenging activity than Ve. It has been shown that the aryl benzofuran amidated derivatives have good antioxidant activity, and particularly, derivatives 5a, 5b, 5c, 6b, 6d and 6e exhibit superoxide anion scavenging activity superior to Ve.

TABLE 3

Evaluation of scavenging activity of aryl benzofuran amidated derivatives on superoxide anion in RAW 264.7

| Compounds | Decrease of 2-OH-E+ (%) |
| --- | --- |
| Ve | 53.18 |
| Salvianolic acid C | 37.82 |
| 5a | 78.59 |
| 5b | 74.16 |
| 5c | 60.54 |
| 6b | 80.81 |

TABLE 3-continued

Evaluation of scavenging activity of aryl benzofuran amidated derivatives on superoxide anion in RAW 264.7

| Compounds | Decrease of 2-OH-E+ (%) |
| --- | --- |
| 6c | 41.65 |
| 6d | 81.27 |
| 6e | 83.41 |

Embodiment 14

The effect of benzofuran amidated derivatives on uric acid production is evaluated using a cell model.

(1) Preparation of the test drug: accurately weigh the appropriate amount of the test drug, and use DMSO to prepare a 10 mM stock solution, and store at 4° C.

(2) Experimental procedure: Normal hepatocyte LO2 are inoculated in a 6-well plate (plate density $1 \times 10^6$ cells/mL), and cell experiments are performed after 4 hours of plating. The experiment is divided into blank group, model group and drug-administered group; the model group and the drug-administered group are respectively added with the modeling agent xanthine (prepared with DMSO as a stock solution), while the blank group is added with the same volume of DMSO, and the Febuxostat is used as a positive control. Take 5 μM of febuxostat, the positive control drug, dilute the test drug with the medium to the required concentration (10 μM, 30 μM, 50 μM), then add them to a 6-well plate, and incubate them at 37° C. for 15 min; add a final concentration of 10 μM xanthine to the model group and the drug-administered group, respectively, and set up two duplicate wells for each group, and set them in a cell culture incubator to culture for 24 hours; collect 100 μL of the culture medium for LC-MS analysis.

(3) Pre-treatment of mass spectrometry: take 100 μL of the medium collected, add MeOH 400 μL, $CHCl_3$ 100 μL and $H_2O$ 300 μL, perform vortex mixing, and centrifuging at 20000 g for 10 min, then take the upper layer for concentration and dry. Reconstitute $H_2O$ 100 μL, and add 10 μL of internal standard substance galantamine (1.25 μM) (final concentration 0.125 μM), centrifuge at 13,000 rpm for 10 min, and take the upper layer for LC-MS analysis.

(3) The results of the assay are shown in Table 4. The aryl benzofuran amidated derivatives 5b, 6e and Salvianolic acid C (1) have a significant inhibitory effect on the formation of uric acid in a hepatocyte model formed by xanthine modeling, and exhibit a certain concentration dependence.

TABLE 4

Inhibition of uric acid in cell model by benzofuran arnidated derivatives 5b, 6e

| Compound | Concentration (μM) | Inhibition rate (%) |
| --- | --- | --- |
| Febuxostat | 5 | 78.7 |
| Satviatiolic acid C (1) | 10 | 15.2 |
|  | 30 | 24.7 |
|  | 50 | 31.4 |
| 5b | 10 | 28.6 |
|  | 30 | 46.1 |
|  | 50 | 62.6 |
| 6e | 10 | 31.5 |
|  | 30 | 41.6 |
|  | 50 | 57.2 |

Embodiment 15

The effect of benzofuran amidated derivatives on blood uric acid in mice is evaluated by an animal model of hyperuricemia induced by potassium oxonate (1) Test animals: Kunming mice are provided by the Test Animals Center of Yangzhou University. Fasting is given 12 h before the drug administration and during the test period, and drinking water is not restricted during the experiment.

(2) Preparation of the test drug: accurately weigh the appropriate amount of the test drug, dissolve it with the corresponding volume of physiological saline until the solution is clear, prepare it as a stock solution, and store it at 4° C. for use.

(3) Experimental procedure: The mice are randomly divided into 9 groups, 10 in each group: (1) normal control group, (2) model group, (3) derivative 5b low dose group: 20 mg/kg, (4) derivative 5b medium dose group: 40 mg/kg, (5) derivative 5b high dose group: 80 mg/kg, (6) derivative 6e low dose group: 20 mg/kg, (7) derivative 6e medium dose group: 40 mg/kg, (8) derivative 6e high dose group: 80 mg/kg, (9) positive control group: allopurinol 20 mg/kg. The test drug is prepared with 0.5% sodium carboxymethylcellulose (CMC-Na) at a suitable concentration; the normal control group of mice are intraperitoneally injected with 0.5% sodium carboxymethylcellulose, and the other groups are injected intraperitoneally with potassium oxonate 300 mg/kg. 1 h later, the mice in the normal control group and the model group are intraperitoneally injected with 0.5% sodium carboxymethylcellulose, and the other groups are intraperitoneally injected with 10 mL/kg of the test drug. 2 hours after the drug administration, 500 μL of blood is taken from the eyeball, placed at room temperature for 1 h, centrifuged at 3000 rpm for 5 min, and the upper serum is stored at −4° C. The uric acid level in the serum of the mice is determined according to the method as specified the uric acid detection kit. At the same time, the livers of the mice are taken out, rinsed with physiological saline; take 100 mg of the livers, add 900 μL of pre-cooled physiological saline to make homogenate, and then centrifuge the mixture, and take the supernatant to determine the activity of xanthine oxidase in the liver homogenate according to the method specified in the kit.

(4) The results of the assay are shown in Table 5. After intraperitoneal injection of potassium oxonate in mice, the level of uric acid in the blood is increased significantly. Compared with the normal group, there is a significant difference, indicating successful modeling. After drug administration, both uric acid levels in the serum and XOD activity in the liver show a certain dose dependency with concentration.

TABLE 5

Effect of derivatives 5b and 6e on hyperuricemia model induced by potassium oxonate in mice

| Group | Serum uric acid value (mg/dl) | Oxidation of xanthine in the liver Enzyme activity (U/g protein) |
|---|---|---|
| Normal control group | 3.16 ± 0.54 | 15.8 ± 1.9 |
| Model group | 4.81 ± 0.66 | 16.1 ± 2.4 |
| Derivative 5b low dose group | 3.87 ± 0.31*[a] | 14.1 ± 2.8** |
| Derivative 5b medium dose group | 3.61 ± 0.25** | 13.7 ± 1.6* |
| Derivative 5b high dose group | 3.30 ± 0.46** | 11.6 ± 1.7** |
| Derivative 6e low dose group | 3.82 ± 0.62** | 14.7 ± 2.2* |
| Derivative 6e medium dose group | 3.54 ± 0.26* | 13.2 ± 2.9* |
| Derivative 6e high dose group | 3.26 ± 0.44** | 11.3 ± 1.6** |
| Positive control group | 3.18 ± 0.50** | 10.2 ± 1.4** |

[a]Comparison between the drug-administered group and the model group:
*$P < 0.05$,
**$P < 0.01$.

Embodiment 16

Figure 3:
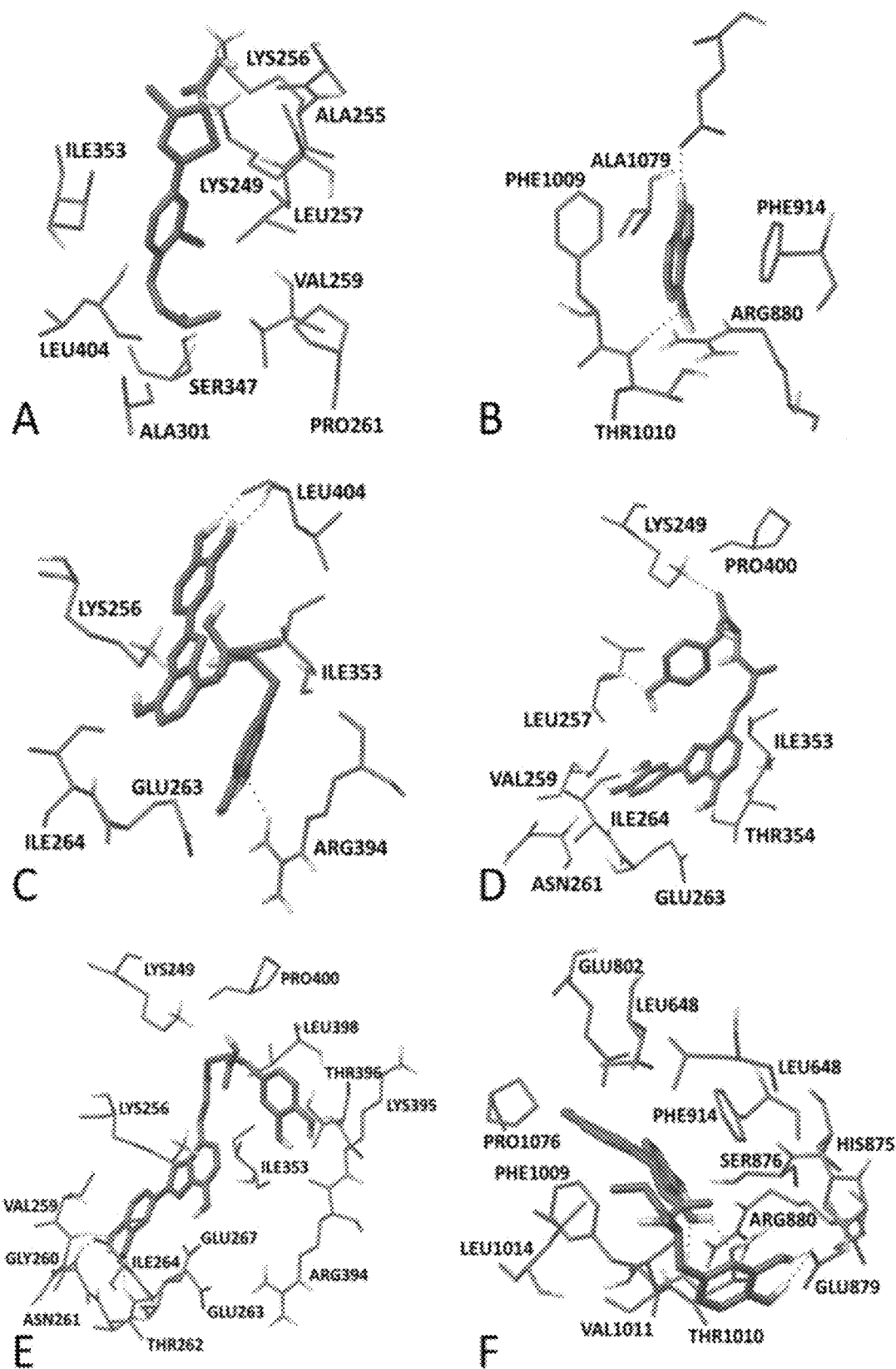
FIG. 3: Results of docking experiments between active compound and xanthine oxidase Detailed explanation for FIG. 3.

In order to preliminarily clarify the possible binding modes and interaction sites of the synthesized 2-aryl benzofuran amidated derivatives with xanthine oxidase, the molecular docking experiment is performed to preliminarily study the mechanism of action of 2-aryl benzofuran amidated derivatives 6e, 6b, 5b and Salvianolic acid (1) with xanthine oxidase. Xanthine oxidase (PDB code: 1F1Q) consists of three subunits A, B, and C, which contain three active domains, which are the Fe/S central domain in the A chain, and the FAD domain in the B chain and Molybdenum pterin domain in the C chain. In the docking experiment, two known xanthine oxidase inhibitors, Febuxostat and Allopurinol, are used as controls. The molecular docking results are analyzed, and it is determined according to the scoring function that the lowest docking conformation of the compound monomer and xanthine oxidase is considered to be its dominant conformation. The docking results are shown in FIG. 3: the docking scores of compounds 1, 6e, 6b, 5b and Febuxostat and Allopurinol are −7.1, −7.42, −7.25, −7.1, −8.19, −5.21, respectively. As can be seen from FIG. 3, compounds 1, 6e, 6b and Febuxostat interact with multiple identical amino acid residues, such as Lys249, Lys256, Leu257, Val259, Ile264, Ile353, Arg394 and Leu404, indicating compounds 1, 6e and 6b may be similar to the positive drug Febuxostat, which binds to the same domain of xanthine oxidase to exert its activity of inhibiting the enzyme. It can also be seen from FIG. 3 that the derivative 5b interacts with the amino acid residues Pro1076, Phe1009, Thr1010, Arg880, Val1011, Leu1014, Glu802, Ser876, Glu879, and forms three hydrogen bonds with the residues Phe1009, Thr1010 and Glu879, which is similar to the positive drug Allopurinol, which may act on the common domain of xanthine oxidase to play the enzyme inhibitory role. It has also been observed that the formation of hydrogen bond and hydrophobic interaction play an important role in stabilizing the conformation of the receptor protein-ligand.

In the results of the docking experiment of the active compound with xanthine oxidase in FIG. 3, (A) Febuxostat (B) Allopurinol (C) 6b (D) 6e (E) Salvianolic acid C (1) (F) 5b.

Embodiment 17

Preparation of Derivative 5b (1) Tablets of the Derivative 5b of the Present Invention:
2 mg of derivative 5b, 88 g of starch and 3 g of magnesium stearate Preparation process: pass the derivative 5b of the present invention through a 100-mesh sieve, add starch and magnesium stearate to mix uniformly, make the mixture into granules, dry and compress it into tablets.

(2) Capsules of the Derivative 5b of the Present Invention
2 mg of derivative 5b, 88 g of starch and 3 g of magnesium stearate Preparation process: pass the derivative 5b of the present invention through a 100-mesh sieve, add starch and magnesium stearate to mix uniformly, make the mixture into granules, dry and capsule it.

(3) Soft Capsule of the Derivative 5b of the Present Invention
10 mg of Derivative 5b and 100 g of soy lecithin Preparation process: take the derivative 5b of the present invention, add soybean soft phospholipid, mill and mix it well, vacuum and press the mixture to receive soft capsules.

(4) The Lyophilized Powder of the Derivative 5b of the Present Invention:
2 g of derivative 5b, 4 g of sodium sulfite and 50 mL of ethanol, dilute to 1000 mL with water;

Preparation process: Take the derivative 5b of the present invention and disperse it in ethanol, dissolve sodium sulfite in water, and gradually add sodium sulfate solution under ultrasonic or stirring to make a clear and transparent solution; make up to a sufficient amount with water; filter through 0.22 μm microporous membrane and lyophilize it to obtain the preparation.

Embodiment 18

Preparation of Derivative 6e (1) Tablets of the Derivative 6e of the Present Invention:
2 mg of derivative 6e, 88 g of starch and 3 g of magnesium stearate Preparation process: pass the derivative 6e of the present invention through a 100 mesh sieve, add starch and magnesium stearate to mix uniformly, make the mixture into granules, dry and compress it into tablets.

(2) Capsules of the Derivative 6e of the Present Invention
2 mg of derivative 6e, 88 g of starch and 3 g of magnesium stearate Preparation process: pass the derivative 6e of the present invention through a 100 mesh sieve, add starch and magnesium stearate to mix uniformly, make the mixture into granules, dry and capsule it.

(3) Soft Capsule of the Derivative 6e of the Present Invention
10 mg of Derivative 6e and 100 g of soy lecithin Preparation process: take the derivative 6e of the present invention, add soybean soft phospholipid, mill and mix it well, vacuum and press the mixture to receive soft capsules.

(4) The Lyophilized Powder of the Derivative 6e of the Present Invention:
2 g of derivative 6e, 4 g of sodium sulfite and 50 mL of ethanol, dilute to 1000 mL with water;

Preparation process: Take the derivative 6e of the present invention and disperse it in ethanol, dissolve sodium sulfite in water, and gradually add sodium sulfate solution under ultrasonic or stirring to make a clear and transparent solution; make up to a sufficient amount with water; filter through 0.22 μm microporous membrane and lyophilize it to obtain the preparation.

The above-mentioned embodiments are illustrative of the representative embodiments of the present invention, and are merely illustrative; the embodiments of the present invention are not limited by the above embodiments, and any other changes, modifications, substitutions, combinations, and simplifications that do not depart from the spirit and principles of the present invention are equivalent replacement and are included in the protection scope of the present invention.

What is claimed is:

1. An aryl benzofuran amidated derivative, wherein a structural formula of the aryl benzofuran amidated derivative is shown in formula I:

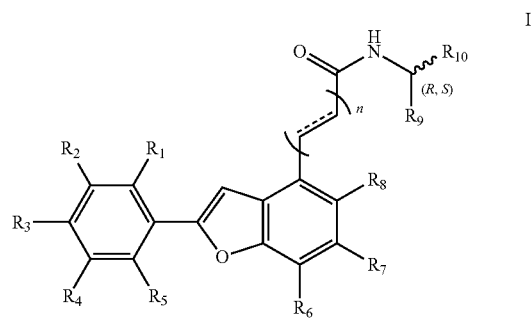

wherein $R_1$, $R_2$, $R_3$, $R_4$, $R_5$, $R_6$, $R_7$, $R_8$ are each independently selected from the group consisting of
hydrogen,
hydroxy,
halogen,
nitro,
benzyl,
$C_{1-4}$ alkyl unsubstituted or substituted with 1 to 3 substituents selected from the group consisting of halogen, hydroxy, nitro and $C_{1-2}$ alkoxy, and
$C_{1-3}$ alkoxy unsubstituted or substituted by 1 to 2 substituents selected from the group consisting of halogen, hydroxy, nitro and $C_{1-2}$ alkoxy;

$R_9$ is one selected from the group consisting of
hydrogen,
$C_{1-4}$ alkyl unsubstituted or substituted with 1 to 3 substituents selected from the group consisting of halogen, hydroxy, $C_{1-3}$ alkyl and $C_{1-2}$ alkoxy,
3-ethyl-1H-indole unsubstituted or substituted by one selected from the group consisting of halogen and hydroxy,
phenyl unsubstituted or substituted by one selected from the group consisting of halogen, hydroxy and $C_{1-2}$ alkoxy, and
benzyl unsubstituted or substituted by one selected from the group consisting of halogen, hydroxy and $C_{1-2}$ alkoxy, wherein the X is one selected from the group consisting of F, Cl, and Br; n is 1, 2 or 3; and $R_{10}$ is one selected from the group consisting of
hydrogen,
—COOH,
—COOCH$_3$,
—COOCH$_2$CH$_3$, —COOCH(CH₃)₂,
—COO(CH₂)₂CH₃, and
C$_{1-4}$ alkyl substituted by 1-3 substituents selected from the group consisting of halogen, hydroxy, C$_{1-3}$ alkyl, and C$_{1-2}$ alkoxy.

2. The aryl benzofuran amidated derivative of claim 1, wherein in the formula:

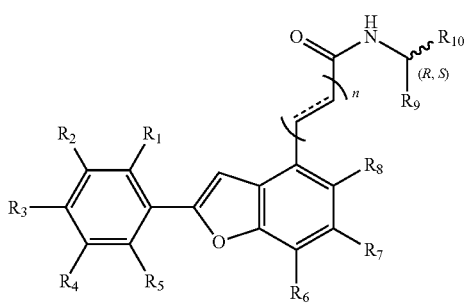

R₃ or/and R₄ are substituents other than hydroxy;
R₉ or/and R₁₀ are substituents other than hydrogen;
or, the aryl benzofuran amidated derivative comprises a structural formula:

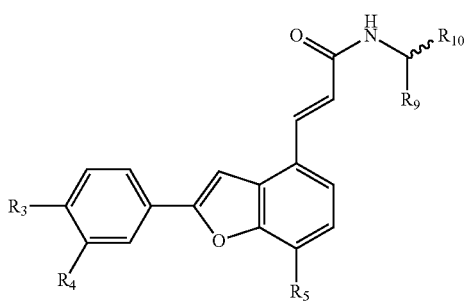

wherein R₃, R₄, and R₆ are each independently C$_{1-3}$ alkoxy unsubstituted or substituted by halogen and hydroxyl;
R₉ is one selected from the group consisting of:
hydrogen,
C$_{1-4}$ alkyl unsubstituted or substituted by one selected from the group consisting of halogen, and hydroxy,
3-ethyl-1H-indole,
phenyl unsubstituted or substituted by one selected from the group consisting of halogen and hydroxy,
benzyl unsubstituted or substituted by one selected from the group consisting of halogen and hydroxy, and
wherein the halogen is one selected from the group consisting of F, Cl, and Br;
R₁₀ is one selected from the group consisting of: hydrogen, —COOH, —COOCH₃, —COOCH₂CH₃, —COOCH(CH₃)₂, —COO(CH₂)₂CH₃, and C$_{1-4}$ alkyl substituted by 1-3 substituents selected from the group consisting of halogen, hydroxy, C$_{1-3}$ alkyl, and C$_{1-2}$ alkoxy;

or, the aryl benzofuran amidated derivative comprises the structural formula:

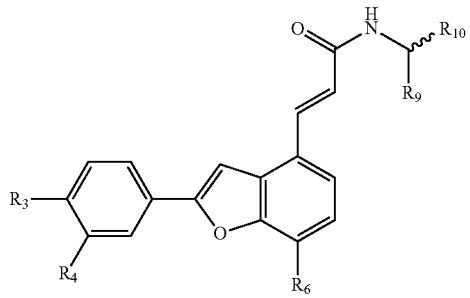

wherein R₃, R₄, and R₆ are each independently hydroxy;
R₉ is hydrogen; R₁₀ is hydrogen;
or, the aryl benzofuran amidated derivative comprises the structural formula:

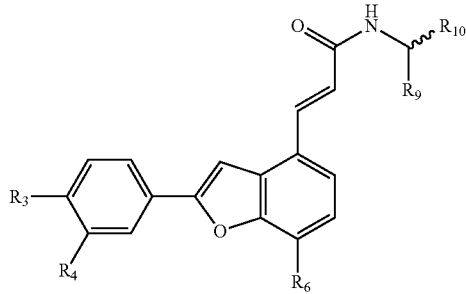

wherein R₃, R₄, and R₆ are each independently C$_{1-3}$ alkoxy unsubstituted or substituted by halogen and hydroxyl;
R₉ is one selected from the group consisting of:
C$_{1-4}$ alkyl unsubstituted or substituted with 1 to 3 substituents selected from the group consisting of halogen, and hydroxy,
3-ethyl-1H-indole unsubstituted or substituted by one selected from the group consisting of halogen and hydroxy,
phenyl unsubstituted or substituted by one selected from the group consisting of halogen and hydroxy,
benzyl unsubstituted or substituted by one selected from the group consisting of halogen and hydroxy, and
wherein the halogen is one selected from the group consisting of F, Cl, and Br; R₁₀ is one selected from the group consisting of: —COON, —COOCH₃, —COOCH₂CH₃, —COOCH(CH₃)₂, —COO (CH₂)₂CH₃ hydrogen, and C$_{1-4}$ alkyl substituted by 1-3 substituents selected from the group consisting of halogen, hydroxy, C$_{1-3}$ alkyl, and C$_{1-2}$ alkoxy.

3. The synthesis method of claim 1, comprising the following steps:
(1) mixing salvianolic acid C with a first inorganic base to obtain a first mixture, ultrasonically dissolving the first mixture in a first organic solvent to obtain a second mixture, and heating the second mixture and continuously detecting a reaction of the second mixture; after the reaction is completed, carrying out a first separation and purification method by silica gel column chromatography to obtain an intermediate Tournefolic acid A;

(2) adding SOCl$_2$ to a second organic solvent under ice bath cooling, and reacting for 30 min to obtain a first solvent, then adding amino compounds selecting from alanine, phenylalanine, cysteine, tyrosine, methionine, tryptophan, and D/L-DOPA to the first solvent to obtain a second solvent, stirring the second solvent at room temperature, concentrating and evaporating the second solvent by a second separation and purification method before washing and drying the second solvent to obtain series of carboxyl-protected amino derivatives;

(3) mixing the intermediate Tournefolic acid A with the series of carboxyl-protected amino derivatives at a mole ratio of 1:(1.1-2) under an action of a condensing agent to be a third mixture, dissolving the third mixture in a third organic solvent to obtain a third solvent, stirring the third solvent at room temperature, and after a reaction and treatment of the third solvent, separating the third solvent by a third separation and purification method by silica gel column chromatography to obtain series of aryl benzofuran amidated derivatives; and (4) adding an second inorganic base to the series of aryl benzofuran amidated derivatives to be a fourth solvent, ultrasonically dissolving the fourth solvent in a fourth organic solvent to be a fourth solvent, stirring the fourth solvent at room temperature or heating the fourth solvent under reflux, and continuously monitoring a reaction of the fourth solvent by thin layer chromatography (TLC), subjecting the fourth solvent to post-treatment, and then passing the fourth solvent through silica gel column chromatography or preparative high performance liquid chromatography for separation and purification to obtain series of high purity benzofuran amidated derivatives;

wherein each of the first separation and purification method and the third separation and purification method is as follows:

performing separation and purification by silica gel column chromatography, mobile phase gradient elution with chloroform/methanol/formic acid; or using preparative liquid chromatography column for the separation and purification of a sample mixture, wherein the preparative liquid chromatography column is an Agilent Zorbax-C18 column with a column length of 250 mm, an inner diameter of 9.4 mm and a particle size of 5 µm, and chromatographic conditions are: flow rate: 8 mL/min, detection wavelength: 281 nm, column temperature: 30° C., mobile phase: acetonitrile—0.1% formic acid—water.

4. The synthesis method of claim 3, wherein the first inorganic base in step (1) is selected from the group consisting of LiOH, NaOH, and KOH, and the first organic solvent is THF, MeOH, H$_2$O and mixed solvent of THF, MeOH and H$_2$O, a reaction time of the first inorganic base and the first organic solvent is 8-12 hours;

the first separation and purification method in step (1) comprises: performing silica gel column chromatography, and then performing isocratic eluting with chloroform, methanol, and formic acid at a ratio of 10:1:0.1 by volume to obtain the intermediate Tournefolic acid A;

the amino compounds in step (2) is an amino acid of various D/L configurations, and the second organic solvent is a reagent and the reagent is methanol, ethanol or isopropanol, and a reaction time of the second organic solvent is 18-24 hours;

the second separation and purification method in step (2) comprises: washing a sample by methanol and diethyl ether alternatively for multiple times, then concentrating and evaporating the sample;

the condensing agent in step (3) is selected from the group consisting of DCC/HoBt, EDCI/HoBt, HATU, HBTU and PyBOP, and the third organic solvent is a mixed solvent DMF/CH$_2$CL$_2$, wherein a ratio of DMF to CH$_2$CL$_2$ ranges from (3:1) to (5:1) by volume, a reaction time of the third organic solvent is 8-12 hours;

the third separation and purification method in step (3) comprises: silica gel column chromatography, gradient eluting with chloroform/methanol to obtain a target derivative; and the second inorganic base in step (4) is LiOH, NaOH, or KOH, and the fourth organic solvent is selected from the group consisting of THF, MeOH, H$_2$O or mixed solvent of THF, MeOH and H$_2$O, a reaction time of the fourth organic solvent is 8 hours to 12 hours.

5. The synthesis method of claim 3, wherein:

L-dopa methyl ester hydrochloride is one of the series of carboxyl-protected amino derivatives with a following structure formula:

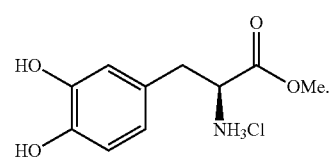

4a

6. The synthesis method of claim 5, wherein:

a preparation method of the L-dopa methyl ester hydrochloride is as follows: accurately taking 5 mL of anhydrous methanol into a 25 mL round bottom flask, cooling in an ice water bath for 15 min, and slowly dripping 493 µL of SOCl$_2$ with a molar concentration of 6.780 mmol into the anhydrous methanol to be a first mixed solvent, stirring the first mixed solvent at 0° C. for 30 min, adding 800 mg of L-DOPA with a molar concentration of 4.520 mmol into the first mixture solvent to obtain a second mixed solvent, reacting the second mixed solvent while stirring for 24 hours at room temperature; after a reaction of the second mixed solvent is completed, evaporating solvent of MeOH and a remaining SOCl$_2$ to be a sample, using MeOH and Et$_2$O to wash the sample alternately several times, concentrating and drying the sample to obtain a reaction product of the L-dopa methyl ester hydrochloride.

7. An aryl benzofuran amidated derivative comprising a structural formula of any of the following:

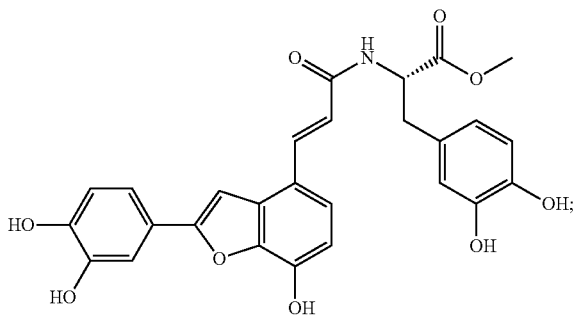

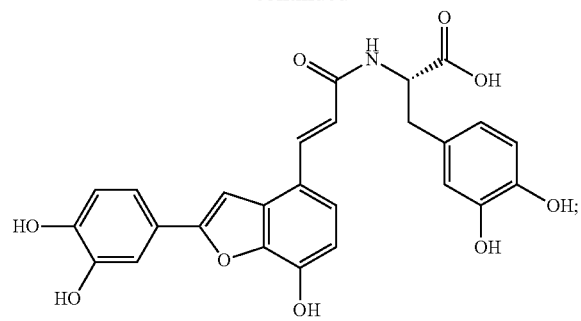
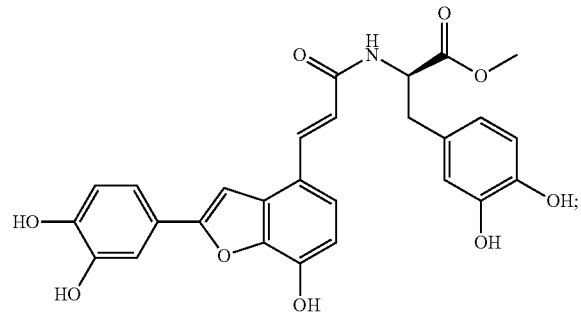
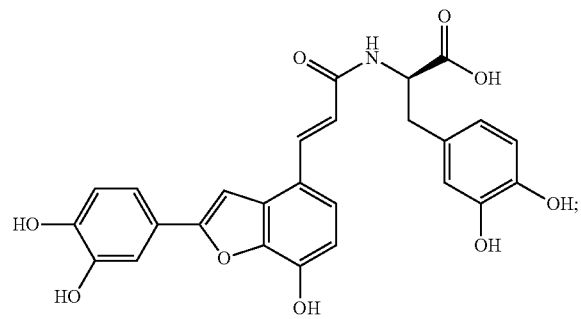
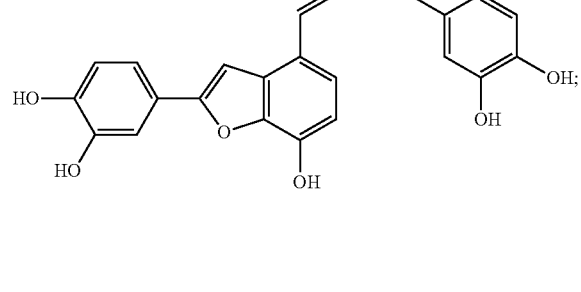
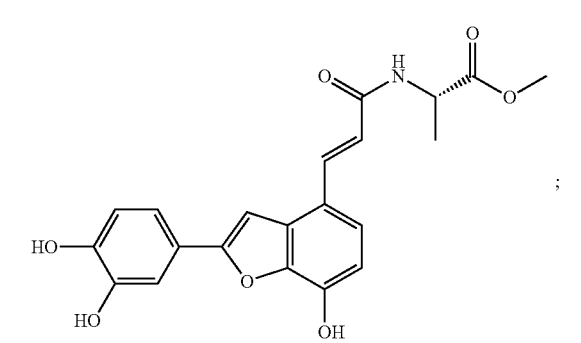
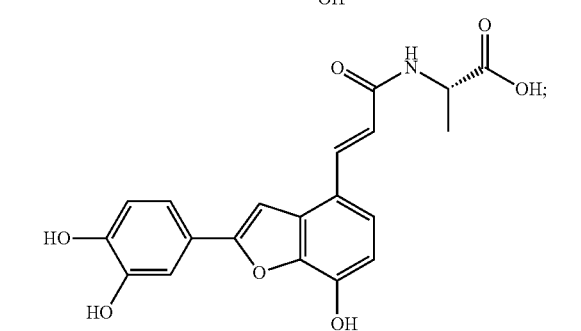
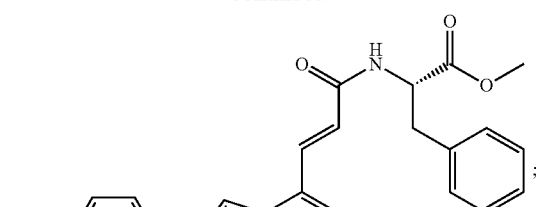
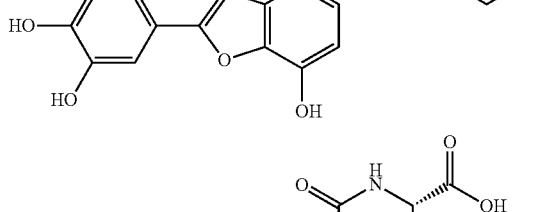
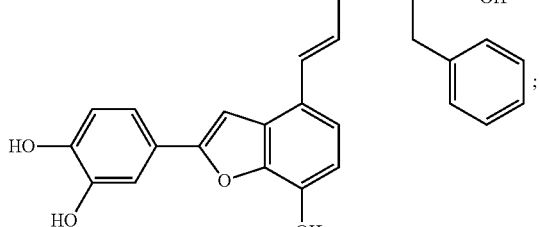
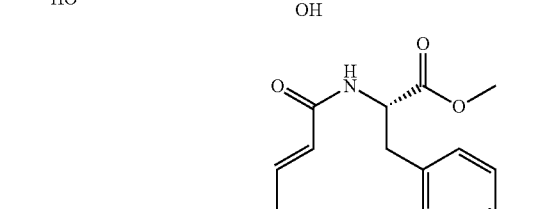
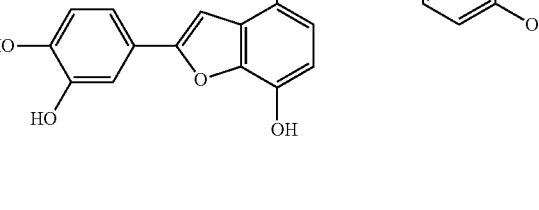
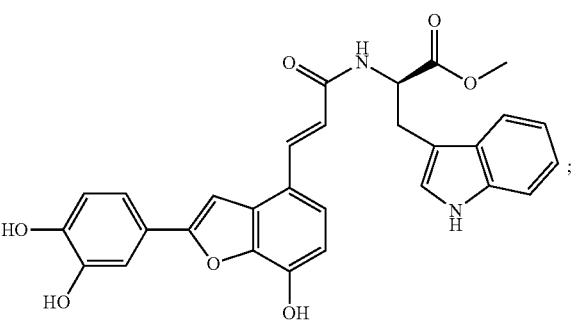

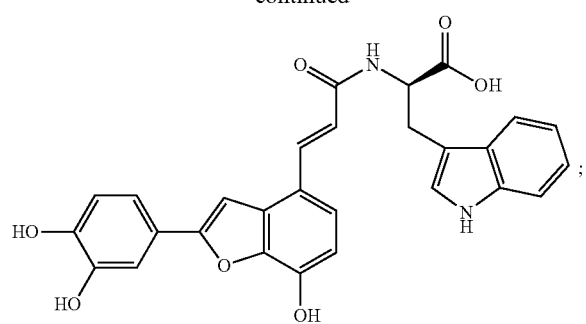
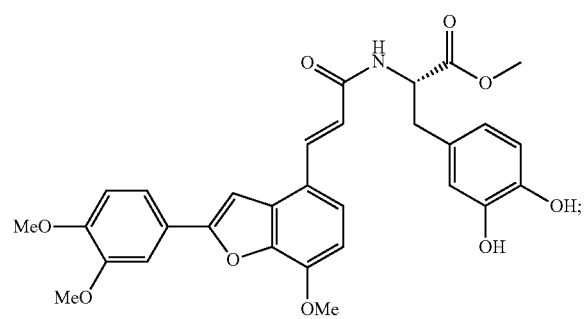
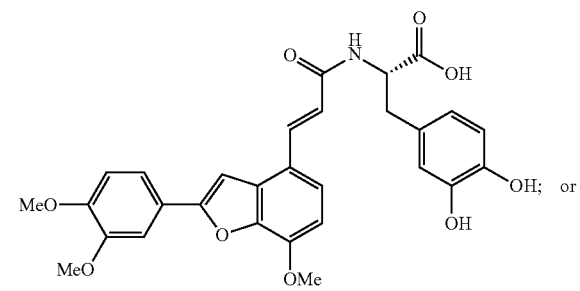
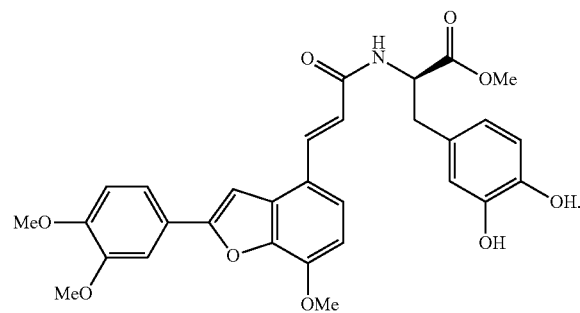
8. An aryl benzofuran amidated derivative comprising a structural formula of any of the following:
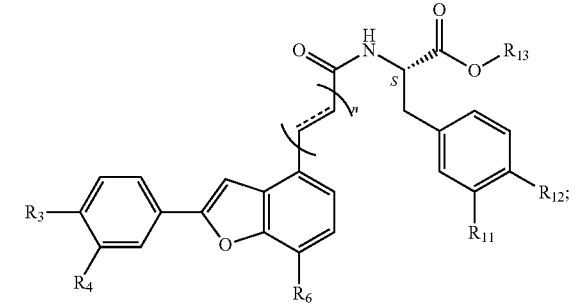
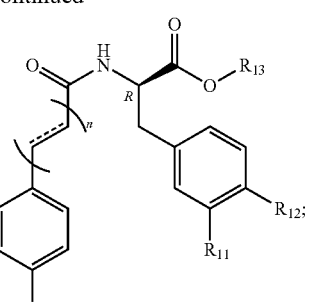
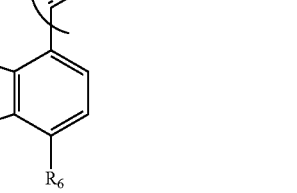
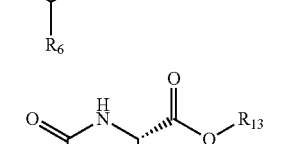
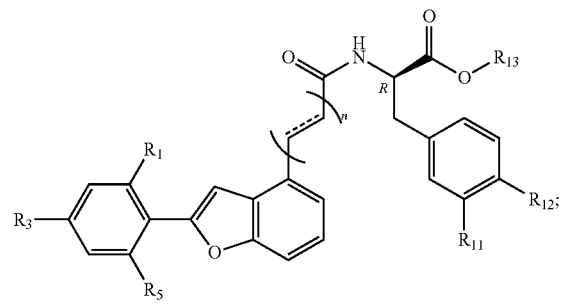

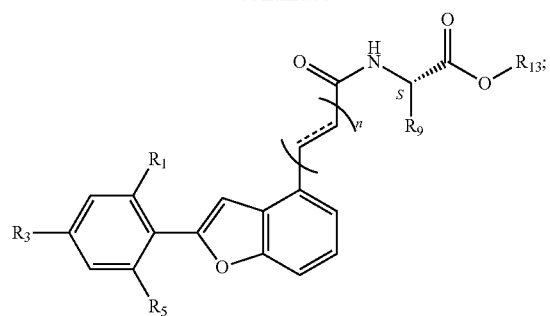

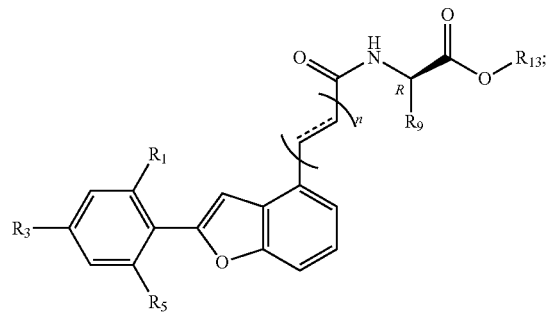

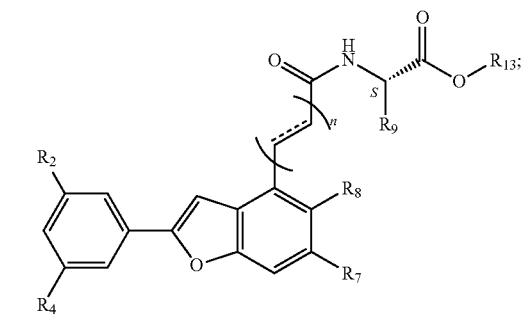

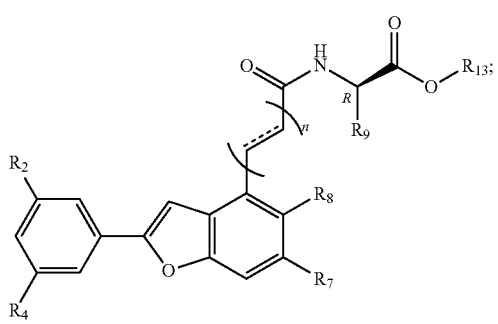

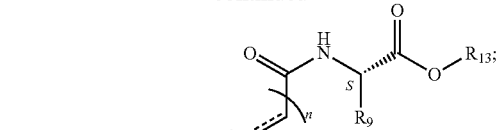

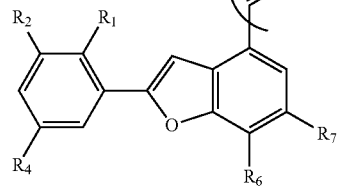

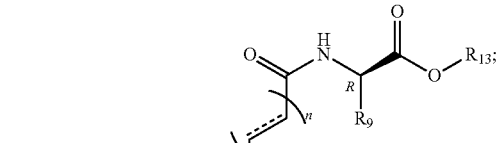

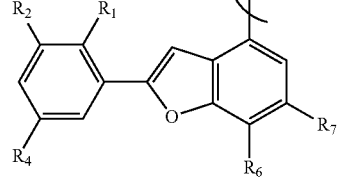

wherein $R_1$, $R_2$, $R_3$, $R_4$, $R_5$, $R_6$, $R_7$, $R_8$, $R_{11}$, and $R_{12}$ are each independently selected from the group consisting of:
hydrogen,
—OH,
—CH$_3$,
—OCH$_3$, and
a halogen selected from the group consisting of F, Cl, and Br; n is 1, 2 or 3;
wherein $R_9$ is selected from the group consisting of:
—CH$_3$,
—OCH$_3$,
—CH$_2$CH$_3$,
—CH(CH$_3$)$_2$,
—(CH$_2$)$_2$CH$_3$; and
wherein $R_{13}$ is selected from the group consisting of:
hydrogen,
—CH$_3$,
—CH$_2$CH$_3$,
—CH(CH$_3$)$_2$,
—(CH$_2$)$_2$CH$_3$, and
a halogen selected from the group consisting of F, Cl, and Br; n is 1, 2 or 3.

* * * * *